US007214658B2

(12) United States Patent
Tobinick

(10) Patent No.: US 7,214,658 B2
(45) Date of Patent: *May 8, 2007

(54) METHOD OF DELIVERING A TNF ANTAGONIST TO THE BRAIN OF A HUMAN BY PERISPINAL ADMINISTRATION WITHOUT DIRECT INTRATHECAL INJECTION

(75) Inventor: Edward L. Tobinick, Los Angeles, CA (US)

(73) Assignee: Tact IP, LLC, Highland Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/016,047

(22) Filed: Dec. 18, 2004

(65) Prior Publication Data

US 2006/0009450 A1   Jan. 12, 2006

Related U.S. Application Data

(60) Provisional application No. 60/585,735, filed on Jul. 6, 2004.

(51) Int. Cl.
   *A61K 38/00* (2006.01)
   *A61K 45/00* (2006.01)
   *A61K 39/00* (2006.01)
   *A61K 39/395* (2006.01)

(52) U.S. Cl. .................. 514/2; 424/145.1; 424/134.1; 424/85.1; 424/1.41; 424/1.49; 435/335

(58) Field of Classification Search ............... None
See application file for complete search history.

(56) References Cited

U.S. PATENT DOCUMENTS

| 5,075,222 | A | 12/1991 | Hannum et al. |
|---|---|---|---|
| 5,574,022 | A | 11/1996 | Roberts et al. |
| 5,605,690 | A | 2/1997 | Jacobs et al. |
| 5,650,396 | A | 7/1997 | Carlino et al. |
| 5,656,272 | A | 8/1997 | Le et al. |
| 5,756,482 | A | 5/1998 | Roberts et al. |
| 5,863,769 | A | 1/1999 | Young |

(Continued)

OTHER PUBLICATIONS

Tobinick et al., Perispinal TNF-alpha inhibition for discogenic pain. Swiss Med Wkly. 2003, 133: 170-177.*
Hetherington et al., Potential for patient harm from intrathetical administration of preserved solutions. Med. J. Aust. 2000, 173: 141-143.*
Valdueza et al., Postural dependency of the cerebral venous outflow. The Lancet 2000, 355:200-201.*

(Continued)

*Primary Examiner*—Janet L. Andres
*Assistant Examiner*—Chang-Yu Wang
(74) *Attorney, Agent, or Firm*—Ezra Sutton, Esq.

(57) ABSTRACT

The present invention provides specific methods of using and administering etanercept to improve cognitive function in a human, for both the treatment and prevention of cognitive impairment, or, alternatively, to enhance cognitive function including Alzheimer's Disease, Idiopathic Dementia, and Traumatic Brain Injury. The methods of the present invention include the perispinal administration of etanercept. For the purposes of this patent "perispinal" is to be considered as referring to "perispinal extrathecal;" therefore direct intrathecal administration is excluded. Perispinal administration leads to enhanced delivery of etanercept to the brain in a therapeutically effective amount, via the vertebral venous system and/or the cerebrospinal fluid. Delivery of etanercept to the brain utilizing the methods of the present invention includes the use of the vertebral venous system to deliver etanercept to the brain via retrograde venous flow. Physical maneuvers are used to enhance delivery of etanercept to the brain via this route.

31 Claims, 6 Drawing Sheets

U.S. PATENT DOCUMENTS

| | | | |
|---|---|---|---|
| 6,013,253 | A | 1/2000 | Martin et al. |
| 6,015,557 | A | 1/2000 | Tobinick et al. |
| 6,096,728 | A | 8/2000 | Collins et al. |
| 6,159,460 | A | 12/2000 | Thompson et al. |
| 6,277,969 | B1 * | 8/2001 | Le et al. .................... 536/23.1 |
| 6,635,250 | B2 | 10/2003 | Olmarker et al. |
| 6,649,589 | B1 | 11/2003 | Olmarker et al. |
| 2003/0148955 | A1 | 8/2003 | Pluenneke |

OTHER PUBLICATIONS

Perry et al. Neurobiol Aging 2001. 22: 873-883.*
Block et al. Prog. Neurobiol. 2005. 76: 77-98.*
Tuppo et al. Int. J. Biochem. Cell Biol. 2005. 37: 289-305.*
Tanzi et al. Neuron 2004. 43: 605-608.*
Gonzales-Scarano et al. Nat. Rev Immunol. 2005. 5: 69-81.*
Tarkowski E, Andreasen N, Tarkowski A, Blennow K. Intrathecal inflammation precedes development of Alzheimer's disease. J Neurol Neurosurg Psychiatry. Sep. 2003;74(9):1200-5.
Tarkowski E, Liljeroth AM, Minthon L, Tarkowski A, Wallin A, Blennow K. Cerebral pattern of pro- and anti-inflammatory cytokines in dementias. Brain Res Bull. Aug. 15, 2003;61(3):255-60. Review.
Tobinick E.L. Targeted etanercept for treatment-refractory pain due to bone metastasis: two case reports. Clin Ther. Aug. 2003;25(8):2279-88.
Tobinick E.L. Targeted etanercept for discogenic neck pain: uncontrolled, open-label results in two adults. Clin Ther. Apr 2003;25(4):1211-8.
Tobinick E.L., Britschgi-Davoodifar S. Perispinal TNF-alpha inhibition for discogenic pain. Swiss Med Wkly. Mar. 22, 2003;133(11-12):170-7.
Tobinick E, Davoodifar S. Efficacy of etanercept delivered by perispinal administration for chronic back and/or neck disc-related pain: a study of clinical observations in 143 patients. Curr Med Res Opin, Jul. 2004; 20(7): 1075-1085.
Genevay S, Stingelin S, Gabay C. Efficacy of etanercept in the treatment of acute, severe sciatica: a pilot study. Ann Rheum Dis Sep. 2004;63:1120-1123.
Tariot PN, Federoff HJ. Current treatment for Alzheimer disease and future prospects. Alzheimer Dis Assoc Disord. Jul.-Sep. 2003;17 Suppl 4:S105-13.
Sheng JG, Bora SH, Xu G, Borchelt DR, Price DL, Koliatsos VE. Lipopolysaccharide-induced-neuroinflammation increases intracellular accumulation of amyloid precursor protein and amyloid beta peptide in APPswe transgenic mice. Neurobiol Dis. Oct. 2003;14(1):133-45.
Chauhan NB, Siegel GJ. Intracerebroventricular passive immunization with anti-Abeta antibody in Tg2576. J Neurosci Res. Oct. 1, 2003;74(1):142-7.
Olmarker K, Rydevik B. Selective inhibition of tumor necrosis factor-[alpha] prevents nucleus pulposus-induced thrombus formation, intraneural edema, and reduction of nerve conduction velocity: possible implications for future pharmacologic treatment strategies of sciatica. Spine Apr. 15, 2001;26(8):863-869.
Brisby M, Olmarker K, Larsson K, Nutu M, Rydevic B. Proinflammatory cytokines in cerebrospinal fluid and serum in patients with disc herniation and sciatica. Eur Spin J Jul. 10, 2001:DOI 10.1007/s005860100306.
Sommer C, Schafers M, Marziniak M, Toyka KV. Etanercept reduces hyperalgesia in experimental painful neuropathy. J Peripher Nerv Syst. 2001; 6(2):67-72.
Aisen PS, Davis KL. Inflammatory mechanisms in Alzheimer's disease: implications for therapy. Am J Psychiatry. Aug. 1994;151(8):1105-13. Review.
Aisen PS, Davis KL. The search for disease-modifying treatment for Alzheimer's disease. Neurology. May 1997;48(5 Suppl 6):S35-41. Review.
Aisen PS, Davis KL, Berg JD, Schafer K, Campbell K, Thomas RG, Weiner MF, Farlow MR, Sano M, Grundman M, Thal LJ. A randomized controlled trial of prednisone in Alzheimer's disease. Alzheimer's Disease Cooperative Study. Neurology. Feb. 8, 2000;54(3):588-93.
Anthony JC, Breitner JC, Zandi PP, Meyer MR, Jurasova I, Norton MC, Stone SV. Reduced prevalence of AD in users of NSAIDs and H2 receptor antagonists: the Cache County study. Neurology. Jun. 13, 2000;54(11):2066-71.
Breitner JC. The role of anti-inflammatory drugs in the prevention and treatment of Alzheimer's disease. Annu Rev Med. 1996;47:401-11. Review.
McGeer PL, Schulzer M, McGeer EG. Arthritis and anti-inflammatory agents as possible protective factors for Alzheimer's disease: a review of 17 epidemiologic studies. Neurology. Aug. 1996;47(2):425-32.
Edsbagge M, Tisell M, Jacobsson L, Wikkelso C. Spinal CSF absorption in healthy individuals. Am J Physiol Regul Integr Comp Physiol 287:R1450-1455, 2004.
Gisolf J, van Lieshout J, van Heusden K, et. al. Human cerebral venous outflow pathway depends on posture and central venous pressure. J Physiol 560.1:317-327(2004).
Ruiz D, Gailloud P, Rufenacht D, et. al. The craniocervical venous system in relation to cerebral venous drainage. Am J Neuroradiol 23:1500-1508, Oct. 2002.
Ibukuro K, Fukuda H, Mori K, Inoue Y. Topographic anatomy of the vertebral venous system in the thoracic inlet. Am J Radiology 176:1059-1065, Apr. 2001.
Batson OV. The function of the vertebral veins and their role in the spread of metastases. Ann Surg 1940:112:138-149.
Batson OV. The vertebral vein system. AJ Radiology 1957 78:195-212.
Anderson R. Diodrast studies of the vertebral and cranial venous systems. J Neurosurg 1951:8:411-422.
Groen R, du Toit D, Phillips F, et. al. Anatomical and Pathological Considerations in Percutaneous Vertebroplasty and Kyphoplasty: A reappraisal of the vertebral venous system. Spine 29(13): 1465-1471 (2004).
Byrod G, Rydevik B, Johansson BR, Olmarker K. Transport of epidurally applied horseradish peroxidase to the endoneurial space of dorsal root ganglia: a light and electron microscopic study. J Peripher Nerv Syst. Dec. 2000:5(4);218-26.
Byrod G, Olmarker K, Konno S, Larsson K, Takahashi K, Rydevik B. A rapid transport route between the epidural space and the intraneural capillaries of the nerve roots. Spine. Jan. 15, 1995;20(2):138-43.
Olmarker K, Larsson K. Tumor necrosis factor alpha and nucleus-pulposus-induced nerve root injury. Spine. Dec. 1, 1998;23(23):2538-44.
Lirk P, Moriggl B, Colvin J, Keller C, Kirchmair L, Rieder J, Kolbitsch C. The incidence of lumbar ligamentum flavum midline gaps. Anesth Analg. Apr. 2004;98(4):1178-80.
Lirk P, Kolbitsch C, Putz G, Colvin J, Colvin HP, Lorenz I, Keller C, Kirchmair L, Rieder J, Moriggl B. Cervical and high thoracic ligamentum flavum frequently fails to fuse in the midline. Anesthesiology. Dec. 2003;99(6):1387-90.
Apkarian Av, Sosa Y, Sonty S, et. al. Chronic back pain is associated with decreased prefrontal and thalamic gray matter density. J Neurosci (2004): 24(46):10410-10415.
Rutgeerts P, Lemmens L, Van Assche G, et. al. Treatment of active Crohn's disease with onercept (recombinant human soluble p55 tumour necrosis factor receptor): results of a randomized, open-label, pilot study. Aliment Pharmacol Ther 2003: 17: 185-192.
Wilson CJ, Finch CE, Cohen HJ,—The case for a head-to-toe inflammatory paradigm. American Geriatrics Society 2002—2041-2056.
Cooper NR, Kalaria RN, McGeer PL, Rogers J.—Key issues in Alzheimer's disease inflammation—Neurobiology of Aging 21—Elsevier Science Inc. 451-453.

* cited by examiner

METHOD OF DELIVERING A TNF ANTAGONIST TO THE BRAIN OF A HUMAN BY PERISPINAL ADMINISTRATION WITHOUT DIRECT INTRATHECAL INJECTION

RELATED APPLICATIONS

This is a non-provisional application claiming the benefit of provisional U.S. Patent Application No. 60/585,735 filed, Jul. 6, 2004, and also claiming the benefit of U.S. patent application Ser. No. 10/269,745, filed, Oct. 9, 2002, now U.S. Pat. No. 6,982,089, which is a continuation-in-part of application Ser. No. 09/841,844, filed on Apr. 25, 2001, now U.S. Pat. No. 6,537,549, issued on Mar. 25, 2003, which is a continuation-in-part of application Ser. No. 09/826,976, filed on Apr. 5, 2001, now U.S. Pat. No. 6,419,944, issued Jul. 16, 2002, which is a continuation-in-part of application Ser. No. 09/654,996, filed on Sep. 5, 2000, now U.S. Pat. No. 6,419,934, issued on July 16, 2002, which is a continuation-in-part of application Ser. No. 09/476,643, filed on Dec. 31, 1999, now U.S. Pat. No. 6,177,077, issued Jan. 23, 2001, which is a continuation-in-part of application Ser. No. 09/275,070, filed on Mar. 23, 1999, now U.S. Pat. No. 6,015,557, issued Jan. 18, 2000, which is a continuation-in-part of application Ser. No. 09/256,388, filed on Feb. 24, 1999, now abandoned.

FIELD OF THE INVENTION

Tumor necrosis factor-alpha (TNF) is a proinflammatory cytokine which is centrally involved in the initiation, maintenance, and amplification of the immune processes which produce neurologic inflammation, and which have been implicated in the pathogenesis of Alzheimer's Disease and other forms of inflammation resulting in neurological damage. Etanercept is a biologic TNF antagonist, a recombinant DNA fusion protein which was designed to directly bind TNF and thereby reduce or eliminate the adverse biologic effects of excess TNF. Etanercept can result in rapid clinical improvement in conditions, such as Alzheimer's Disease, characterized by TNF-mediated neuronal inflammation and excess TNF.

The present invention provides specific methods of using and administering etanercept and/or other TNF binding biologics to improve cognitive function in a human, for both the treatment and prevention of cognitive impairment, or, alternatively, to enhance cognitive function in three different broad categories of conditions:

1. Cognitive impairment which is characteristic of certain neurological disorders (for example Alzheimer's Disease, Idiopathic Dementia, and Traumatic Brain Injury);
2. Cognitive impairment which accompanies certain systemic or localized non-neurological conditions which are known or suspected to be associated with increased TNF (for example rheumatoid arthritis, psoriasis, and cancer cachexia); and
3. To enhance cognitive function in individuals in whom there is either no brain pathology or in whom the existence of brain pathology is either unknown or undefined, including a human without known disease.

The pathological conditions included in category 1 above include dementia or cognitive impairment suspected or established to be due to Alzheimer-type pathology, including Mild Cognitive Impairment, Possible Alzheimer's Disease, Probable Alzheimer's Disease, Alzheimer's Disease, and Senile Dementia/Alzheimer's type; Idiopathic Dementia or Dementia of unknown cause; Dementia with Lewy Bodies, also called Diffuse Lewy Body Disease; Picks Disease and other forms of frontotemporal dementia; cognitive impairment due to traumatic brain injury; AIDS (HIV) Dementia; and Vascular Dementia. Cognitive impairment known to be due to infectious agents other than HIV or to brain tumors, either primary or metastatic, are not the subject of this patent.

Category 2 conditions include those medical conditions known to be associated with increased TNF, and specifically include rheumatoid arthritis, juvenile rheumatoid arthritis, psoriasis, psoriatic arthritis, and ankylosing spondylitis, and, in addition, cancer cachexia or cancer metastatic to the spine. Also included in Category 2 is chronic back pain.

Category 3 includes normal individuals, without a known disease or disorder that has been established to be associated with elevated levels of TNF, who desire to achieve enhanced cognitive function.

The methods of the present invention include not only the perispinal administration of etanercept (which itself can be accomplished in various ways, including transcutaneous interspinous injection, or catheter delivery into the epidural or interspinous space) but also other novel methods of localized administration, specifically including intranasal administration.

Perispinal administration involves anatomically localized delivery performed so as to place the therapeutic molecule directly in the vicinity of the spine at the time of initial administration. For the purposes of this patent the "interspinous space" is defined as the anatomic region, including the subcutaneous and deeper areas, which is between two adjacent spinous processes but is external to the ligamentum flavum, which delimits the epidural space (see FIG. 1). For the purposes of this patent, "in the vicinity of" is defined as within 10 centimeters. Perispinal administration includes, but is not limited to, the following types of administration: parenteral; subcutaneous; intramuscular; interspinous; epidural; and specifically includes, but is not limited to:

1. The use of a percutaneous injection carried through the skin in the midline of the neck or back, directly overlying the spine, to deliver etanercept into the subcutaneous or deeper portion of the interspinous space;
2. Percutaneous epidural injection, to deliver etanercept directly into the epidural space;
3. Administration of etanercept via an indwelling epidural catheter which delivers etanercept to the epidural space; and,
4. Via an indwelling interspinous catheter which delivers etanercept to the interspinous space.

For the purposes of this patent perispinal administration excludes intrathecal administration, which carries additional risks of infection and hemorrhage. Therefore in this patent "perispinal" is more exactly defined as "perispinal (extrathecal)", but for the purposes of brevity shall be designated throughout simply as "perispinal". Perispinal administration leads to enhanced delivery of etanercept to the brain in a therapeutically effective amount. The conventional mode of delivery of etanercept for rheumatologic applications, i.e. subcutaneous administration in the abdomen, thighs, or arms, is not perispinal administration, and does not cause efficient delivery of etanercept to the brain and is therefore distinguished from the perispinal methods of administration of etanercept described in this invention, including the four methods described above.

Enhanced delivery of etanercept to the brain via perispinal administration is possible because of unique anatomic pathways that are present in the perispinal area, both in the neck and in the back. These unique anatomic conditions include the following:

1. The presence of a richly anastomosed and valveless vertebral venous system, comprised of the external vertebral venous plexus interconnected with the internal vertebral venous plexus, which surrounds the spinal cord and spinal column, into which drain the subcutaneous veins which drain the interspinous space;
2. The presence of the thecal sac, containing the cerebrospinal fluid (CSF), within which the spinal cord floats, inside the vertebral column;
3. A direct fluid connection between both of these spinal systems and the brain, since the spinal CSF circulates and directly bathes the brain, and the vertebral venous system is directly connected to the cranial veins, into which the vertebral veins drain, in a retrograde fashion, when the patient is properly positioned; and,
4. The location of the spine within reasonable proximity of the skin surface, allowing etanercept delivered by percutaneous needle administration into the interspinous space to reach the brain via the vertebral venous system and the CSF in a therapeutically effective quantity.

Because of this unique confluence of anatomic conditions, the vertebral venous system represents a "back door" for delivery of therapeutic molecules to the brain. Since the vertebral venous system is valveless, flow to the brain after perispinal administration is possible, and is augmented by physical maneuvers which are part of this invention and are elaborated herein. Biologics, such as etanercept, which, because of their recombinant origin, possess extraordinary therapeutic potency and immediate efficacy, are particularly suited to delivery via this route. Although previously recognized as a possible route by which prostate and other remote cancers may reach the brain, the vertebral venous system has not previously been recognized as a route for delivery of therapeutic molecules to the brain.

Midline interspinous administration of etanercept is demonstrated herein to produce improvement in cognitive function in individuals with Mild Cognitive Impairment and Senile Dementia/Alzheimer's type. In addition to percutaneous injection into the interspinous or epidural space, etanercept may also be delivered to the interspinous or epidural space by implantable catheter, with the catheter reservoir placed remotely, such as in the abdominal area.

For the purposes of this invention "improvement in cognitive function" is defined as improvement in any of the following: memory, attention, perception, learning, thought, concept formation, reading, problem solving, and related behavior.

The anatomic route which enables the efficient delivery of perispinal etanercept to the brain is identified herein by the inventor, and physical maneuvers to facilitate this process are described herein. For the purposes of this patent perispinal etanercept is distinguished from the use of etanercept delivered by subcutaneous administration at anatomic sites, such as the abdomen, thighs, and arms, which are remote from the spine.

In addition to using etanercept there are two non-monoclonal antibody biologic TNF binding proteins disclosed in this patent to use: onercept (Serono) and pegylated soluble TNF receptor type 1 (Amgen).

BACKGROUND OF THE INVENTION

All of the cytokine antagonists which are currently available have been developed for systemic administration. This is because all were developed to treat systemic illnesses, including rheumatoid arthritis, juvenile rheumatoid arthritis, psoriatic arthritis, or Crohn's Disease.

The use of cytokine antagonists to treat neurological disorders is discussed in several previous patents of this inventor, including U.S. Pat. Nos. 6,015,557, 6,177,077, 6,419,944 B2, 6,537,549 and U.S. patent application 20030049256 of this inventor. These issued patents and patent applications are incorporated in their entirety herein.

The adverse biologic effects of excess TNF can be reduced by the use of biologic inhibitors of TNF. These inhibitors can be divided into two broad categories: monoclonal antibodies and their derivatives; and TNF binding biologics which are not antibody based. In the first category belong infliximab (Remicade®, Centocor), adalimumab (Humira®, Abbott), and CDP 870 (Celltech). All of these monoclonal antibody based anti-TNF biologics are clearly distinct from the TNF binding proteins of this invention, both functionally and biologically. For example, both adalimumab and infliximab have the ability to lyze cells directly, a property which is not shared by etanercept, and a property which is not advantageous for the present invention. In fact the ability to lyze cells is deleterious for CNS applications. The second category includes etanercept, pegylated soluble TNF receptor type 1 (Amgen) and onercept (Serono). The uses of etanercept, pegylated soluble TNF receptor type 1 and onercept for the purposes of this patent are therefore distinguished from those of both adalimumab and infliximab, and other monoclonal antibody-derived anti-TNF products in development, such as CDP 870.

The biologic TNF inhibitors which are the subject of this patent are the non-monoclonal antibody TNF biologics. The three products of this type which have advanced the furthest in development are etanercept, a fusion protein which contains two p75 soluble TNF receptors fused to an Fc fragment of an IgG1 immunoglobulin; and two distinct p55 receptor derivatives: pegylated soluble TNF receptor type 1 and onercept, also referred to as TNF-binding protein-1. Etanercept has a serum half life of approximately 4.8 days when administered to patients with rheumatoid arthritis on a chronic basis; onercept has a serum half-life which is considerably shorter, and it is usually administered at least three times weekly when used to treat systemic illnesses.

Perispinal administration of a TNF binding biologic when compared to systemic administration, carries with it one or more of the following advantages for the present invention:

1) greatly improved efficacy due to improved delivery of the therapeutic molecule to the brain via both the vertebral venous system (VVS) and the CSF.
2) greater efficacy due to the achievement of higher local concentration in the interspinous space, leading to improved delivery to the VVS and the CSF.
3) greater efficacy due to the ability of the administered therapeutic molecule to reach the brain without degradation caused by hepatic or systemic circulation;
4) more rapid onset of action;
5) longer duration of action; and
6) Potentially fewer side effects, due to lower required dosage.

Clinical experience utilizing perispinal administration of etanercept for treating lumbar and cervical radiculopathy and other forms of neuropathic pain caused by vertebral disc disease has demonstrated the dramatic efficacy, and the extraordinarily rapid onset of action produced by perispinal administration of etanercept for these disorders (see Tobinick references 14, 15, and 16). Etanercept, in part due to its molecular weight, has difficulty in crossing the blood-brain barrier when administered systemically. In this invention perispinal administration of etanercept provides a route of administration which allows etanercept to bypass the blood-brain barrier and/or blood-nerve barrier in therapeutic amounts for treating the neurological conditions of consideration herein when it is administered in therapeutic doses of 25 mg to 100 mg to the interspinous space, or in even lower dosage if delivered directly to the epidural space.

Specific inhibitors of TNF, only recently commercially available, now provide the possibility of therapeutic intervention in TNF mediated disorders. These agents have been developed to treat systemic illnesses, and therefore have been developed for systemic administration. Various biopharmaceutical companies have developed TNF antagonists to treat systemic illnesses: Immunex Corporation developed etanercept (Enbrel®) to treat rheumatoid arthritis and Serono is developing onercept, a recombinant TNF binding protein (r-TBP-1) for treating rheumatoid arthritis and psoriasis/psoriatic arthritis.

Etanercept can also be designated as TNFR:Fc because it is a dimeric fusion protein consisting of two soluble TNF receptors fused to a Fc portion of an immunoglobulin molecule. This fusion protein functions in a manner quite distinct from a simple soluble TNF receptor. Soluble TNF receptors are normally present in the human body. But the use of these soluble TNF receptors as therapeutic agents for the treatment of the conditions of consideration in this patent is made impractical by their extremely short half-life and therefore their limited biologic activity. The present invention utilizing etanercept is therefore distinguished from an invention specifying the use of a soluble TNF receptor. It is incorrect and imprecise to describe etanercept as a soluble TNF receptor because this is an incorrect description of its complex structure and omits characteristics of etanercept which are absolutely essential to its biological functions, including the avidity of its binding to TNF. This is further underscored by the developmental history of etanercept. In its first iteration the precursor molecule to etanercept was produced with a single TNF receptor fused to an immunoglobulin fragment. The biologic activity of this molecule was poor. Therefore not only is etanercept distinguished from a soluble TNF receptor, it is also distinguished from a TNF-binding fusion protein which contains the recombinant DNA sequence of only a single soluble TNF receptor. The unique structure of etanercept, containing a dimer (two) soluble TNF receptors fused to an Fc portion of an immunoglobulin molecule, is necessary for the proper performance of the present invention. Since etanercept has the molecular structure of a fusion protein it is thus quite distinct from both onercept and pegylated soluble TNF receptor type 1.

DESCRIPTION OF THE PRIOR ART

U.S. Pat. No. 6,277,969 discloses the use of anti-TNF antibodies for treatment of various disorders. However, it does not disclose administering etanercept by the perispinal route as a way of treating or preventing cognitive impairment due to the dementing disorders of the present invention.

U.S. Pat. No. 5,656,272 to LE et. al. discloses the use of TNF inhibitors for treatment of various disorders, including the use of anti-TNF monoclonal antibodies. However, it does not disclose administering etanercept by the perispinal route as a way of treating or preventing cognitive impairment due to the dementing disorders of the present invention.

U.S. Pat. No. 5,650,396 discloses a method of treating multiple sclerosis (MS) by blocking and inhibiting the action of TNF in a patient. However, it does not disclose administering etanercept by the perispinal route as a way of treating or preventing cognitive impairment due to the dementing disorders of the present invention.

U.S. Pat. No. 5,605,690 discloses the use of TNF inhibitors for treatment of various disorders. However, it does not disclose administering etanercept by the perispinal route as a way of treating or preventing cognitive impairment due to the dementing disorders of the present invention.

U.S. patent application U.S. 2003/0148955 to Pluenneke discloses the use of biologic TNF inhibitors, including etanercept, for the treatment of medical disorders. However, it does not give an enabling disclosure of the use of etanercept for the treatment of Alzheimer's Disease utilizing the perispinal route as does the present invention and it does not predate the U.S. Pat. No. 6,015,557 of the present inventor of which this patent application is a continuation-in-part.

U.S. Pat. Nos. 6,649,589 and 6,635,250 to Olmarker, and previous publications by Olmarker (Olmarker references 25 and 53) discuss the use of TNF inhibitors for the treatment of nerve root injury and related disorders. However they do not disclose administering etanercept for the treatment of Alzheimer's Disease, dementia, or Mild Cognitive Impairment.

The use of prednisone, non-steroidal anti-inflammatory agents, and other anti-inflammatory agents (not including etanercept) has been proposed and studied for the treatment of Alzheimer's Disease (see references 28–33), but none of these studies has been successful, and none of these articles or studies disclosed the methods of the present invention.

Two articles by Byrod discussed a mechanism whereby substances applied epidurally can cross into the endoneurial space (Byrod references 51 and 52), but neither article discusses the perispinal use of etanercept for the treatment of Alzheimer's Disease, dementia, or mild cognitive impairment.

Two recent articles (Lirk references 54 and 55) discuss an anatomic finding, disclosing the existence of a gap in a ligamentous barrier to the epidural space. These articles, however, do not discuss the administration of etanercept by the perispinal route, or the relevance of this anatomic finding to the delivery of perispinal etanercept to the VVS and the cerebrospinal fluid.

Two recent articles by Tarkowski, et. al. identify elevated levels of TNF in the CSF of patients with MCI and AD (references 11 and 12). Tarkowski, however, proposes that these elevated TNF levels may be neuroprotective and therefore does not propose the use of etanercept or other anti-TNF biologic for the treatment of these conditions.

Batson in 1940 (reference 47) published information regarding the vertebral venous system. Experimentally he demonstrated a connection between the pelvic venous system and the vertebral venous system, and proposed that this was a route whereby carcinoma originating in the pelvis could metastasize to the brain. His work did not disclose the methods of the present invention for treatment of Alzheimer's Disease and related disorders.

Ruiz and Gisolf (references 44 and 45) have recently published articles discussing the vertebral venous system and its connections to the cranial venous system. Neither authors discuss the potential use of this system as a route of administration of biologics or pharmaceuticals for delivery to the brain.

Retrograde cerebral perfusion has been previously demonstrated to deliver dye to the surface of the brain in pigs after superior vena caval injection (Ye reference 42)) but the authors did not propose the use of this route to deliver therapeutic molecules to the brain.

Several authors (references 44–50) have discussed the anatomy and function of the vertebral venous system but none have proposed the use of the vertebral venous system as a route of drug delivery to the brain, nor have they proposed the methods of the present invention utilizing etanercept for the treatment of cognitive impairment.

Rutgeerts (reference 58) has discussed the use of onercept to treat Crohn's disease but they have not proposed the methods of the present invention utilizing onercept for the treatment of cognitive impairment.

Pharmacologic chemical substances, compounds and agents which are used for the treatment of neurological disorders, trauma, injuries and compression having various organic structures and metabolic functions have been disclosed in the prior art. For example, U.S. Pat. Nos. 5,756,482 and 5,574,022 to ROBERTS et al disclose methods of attenuating physical damage to the nervous system and to the spinal cord after injury using steroid hormones or steroid precursors such as pregnenolone, and pregnenolone sulfate in conjunction with a non-steroidal anti-inflammatory substance such as indomethacin. These prior art patents do not teach the use of specific cytokine antagonists administered by the perispinal route as a way of treating dementia, as in the present invention.

U.S. Pat. No. 5,863,769 discloses using IL-1 RA for treating various diseases. However, it does not disclose administering etanercept by the perispinal route as a way of improving cognitive function.

U.S. Pat. No. 6,013,253 discloses using interferon and IL-1 RA for treating multiple sclerosis. However, it does not disclose administering etanercept by the perispinal route as a way of improving cognitive function.

U.S. Pat. No. 5,075,222 discloses the use of IL-1 inhibitors for treatment of various disorders. However, it does not disclose administering etanercept by the perispinal route as a way of improving cognitive function.

U.S. Pat. No. 6,159,460 discloses the use of IL-1 inhibitors for treatment of various disorders. However, it does not disclose administering etanercept by the perispinal route as a way of improving cognitive function.

U.S. Pat. No. 6,096,728 discloses the use of IL-1 inhibitors for treatment of various disorders. However, it does not disclose administering etanercept by the perispinal route as a way of improving cognitive function.

Etanercept, in its commercially available form as Enbrel®, is supplied as a powder contained in a vial, with a separate syringe filled with sterile water to which 0.9% benzyl alcohol has been added as a preservative. Etanercept diluted with plain sterile water, not containing benzyl alcohol, is not commercially distributed. The benzyl alcohol increases the shelf life of the Enbrel product, but is not necessary as an active ingredient for the present invention; in several versions of preferred embodiments of the invention benzyl alcohol is omitted intentionally.

None of the prior art patents disclose or teach the use of localized administration of etanercept as in the present invention as a way of treating dementia, in which etanercept provides the patient with a better opportunity to heal, slows disease progression, improves cognitive function or otherwise improves the patient's health.

Accordingly, it is an object of the present invention to provide etanercept administered through the perispinal route as a new method of biologic treatment of neurological conditions which cause dementia such that the use of these biologics will result in cognitive improvement or will slow neurological deterioration.

Another object of the present invention is to provide etanercept for providing suppression and inhibition of the action of specific cytokines in a human to treat neurological or neuropsychiatric diseases or disorders which cause dementia.

Another object of the present invention is to provide etanercept for providing suppression and inhibition of the action of specific cytokines in a human to treat AIDS Dementia, and thereby produce clinical improvement and/or slow disease progression.

Another object of the present invention is to provide etanercept so that it is delivered to the brain in a therapeutically effective dose and thereby improves cognitive function.

An object of several of the variations of the present invention is to provide etanercept, delivered by perispinal administration without the inclusion of benzyl alcohol, for the treatment of a human with chronic neurological disorders of the CNS, such that the human will experience clinical improvement or experience delay of disease progression.

Another object of the present invention is to provide etanercept that produces biologic effects in patients with neurological or neuropsychiatric diseases or disorders by inhibiting the action of TNF and the subsequently occurring inflammatory cascade in the human body for the immediate, short term (acute conditions) and long term (chronic conditions), such that these biologic effects will produce clinical improvement in the patient and will give the patient a better opportunity to heal, improve cognitive function, slow disease progression, prevent neurological damage, or otherwise improve the patient's health.

SUMMARY OF THE INVENTION

The present invention provides specific methods of using and administering etanercept to improve cognitive function in a human, for both the treatment and prevention of cognitive impairment, or, alternatively, to enhance cognitive function in three different broad categories of conditions:

1. Cognitive impairment which is characteristic of certain neurological disorders (for example Alzheimer's Disease, Idiopathic Dementia, and Traumatic Brain Injury);
2. Cognitive impairment which accompanies certain systemic or localized non-neurological conditions which are known or suspected to be associated with increased TNF (for example rheumatoid arthritis, psoriasis, and cancer cachexia); and
3. To enhance cognitive function in individuals in whom there is either no brain pathology or in whom the existence of brain pathology is either unknown or undefined, including a human without known disease.

The pathological conditions included in category 1 above include dementia or cognitive impairment suspected or established to be due to Alzheimer-type pathology, including Mild Cognitive Impairment, Possible Alzheimer's Disease, Probable Alzheimer's Disease, Alzheimer's Disease, and Senile Dementia/Alzheimer's type; Idiopathic Dementia or Dementia of unknown cause; Dementia with Lewy Bodies, also called Diffuse Lewy Body Disease; Picks Disease and other forms of frontotemporal dementia; cognitive impairment due to traumatic brain injury; AIDS (HIV) Dementia and Vascular Dementia. Cognitive impairment known to be due to infectious agents other than HIV or to brain tumors, either primary or metastatic, are not the subject of this patent.

Category 2 conditions include those medical conditions known to be associated with increased TNF, and specifically include rheumatoid arthritis, juvenile rheumatoid arthritis, psoriasis, psoriatic arthritis, and ankylosing spondylitis, and, in addition, cancer cachexia or cancer metastatic to the spine. Also included Category 2 is chronic back pain.

Category 3 includes normal individuals, without a known disease or disorder that has been established to be associated with elevated levels of TNF, who desire to achieve enhanced cognitive function.

The methods of the present invention include not only the perispinal administration of etanercept (which itself can be accomplished in various ways, including transcutaneous interspinous injection, or catheter delivery into the epidural or interspinous space) but also other novel methods of localized administration, specifically including intranasal administration. For the purposes of this patent "perispinal" is to be considered as referring to "perispinal extrathecal"; therefore direct intrathecal administration is excluded from the methods discussed.

Perispinal administration involves anatomically localized delivery performed so as to place the therapeutic molecule directly in the vicinity of the spine, and, for the purposes of this patent, administration which is outside of the intrathecal space (although subsequent movement of the therapeutic molecule into the intrathecal space does occur). Perispinal administration includes, but is not limited to, the following types of administration: parenteral; subcutaneous; intramuscular; interspinous; epidural; or peridural, and specifically includes the use of interspinous injection carried through the skin in the midline of the neck or back, directly overlying the spine; or administration via an indwelling epidural catheter, or via an indwelling catheter which delivers etanercept to the interspinous space. Perispinal administration leads to enhanced delivery of etanercept to the brain in a therapeutically effective amount, via the vertebral venous system and/or the cerebrospinal fluid. Delivery of etanercept to the brain utilizing the methods of the present invention includes the use of the vertebral venous system to deliver etanercept to the brain via retrograde venous flow. In addition to percutaneous injection into the interspinous space, etanercept may also be delivered to the interspinous or epidural space by implantable catheter, with the catheter reservoir placed remotely, such as in the abdominal area. Physical maneuvers are used to enhance delivery of etanercept to the brain via this route.

In addition to etanercept there are two non-monoclonal antibody biologic TNF binding proteins of consideration in this patent: onercept (Serono) and pegylated soluble TNF receptor type 1 (Amgen).

This invention is distinguished from the prior art in a variety of ways, including the use and description of novel and useful new uses, methods of use, and concepts involving TNF binding biologics, including:

1. Novel uses of TNF binding biologics to improve cognitive impairment or produce cognitive enhancement; and
2. Novel methods of use of TNF binding biologics; and
3. Novel concepts, including:
    a. Perispinal (extrathecal) administration distinguished from systemic forms of administration and intrathecal administration;
    b. The use of non-monoclonal antibody anti-TNF biologics as distinguished from the use of monoclonal antibody TNF biologics;
    c. Intranasal administration of TNF binding biologics as a method of delivery to the CNS;
    d. The use of TNF binding biologics to reduce cognitive impairment;
    e. The use of TNF binding biologics for cognitive inhancement;
    f. The use of the vertebral venous system to deliver therapeutic molecules to the brain;
    g. The use of physical maneuvers to facilitate delivery of therapeutic molecules to the brain;
    h. The use of physical maneuvers to influence the direction of venous flow within the cranio-vertebral venous system and thereby deliver therapeutic molecules to the site of neuronal inflammation;
    i. The use of retrograde venous perfusion to deliver therapeutic molecules to the brain, dorsal root ganglion, nerve roots, and spinal cord;
    j. The use of retrograde venous perfusion via the cranio-vertebral venous system to allow therapeutic molecules to bypass the blood-brain barrier and therefore reach the brain;
    k. The use of defects in the ligamentum flavum to facilitate delivery of perispinally administered etanercept to reach the epidural space;
    l. The use of the cranio-vertebral venous system as a "back door" to facilitate delivery of therapeutic molecules to the brain, brainstem, meninges, spinal cord, dorsal root ganglion, and nerve roots;
    m. The use of perispinal administration to introduce etanercept into the interspinous space or the epidural space to enable etanercept to reach the vertebral venous system;
    n. The use of perispinal administration to introduce etanercept into the interspinous space or the epidural space to enable etanercept to reach the cerebrospinal fluid;
    o. The use of etanercept, a dimeric fusion protein, as distinguished from a simple soluble TNF receptor, to produce prolonged improvement in cognitive function;
    p. The use of etanercept delivered by perispinal administration to produce cognitive improvement or to slow disease progression in certain neurological disorders characterized by progressive dementia and TNF-mediated brain inflammation (such as Alzheimer's Disease);
    q. The use of etanercept delivered by intranasal administration as a method to enable it to cross the blood-brain barrier and thereby be used to improve cognitive function.

OVERALL DESCRIPTION

Figure 1:
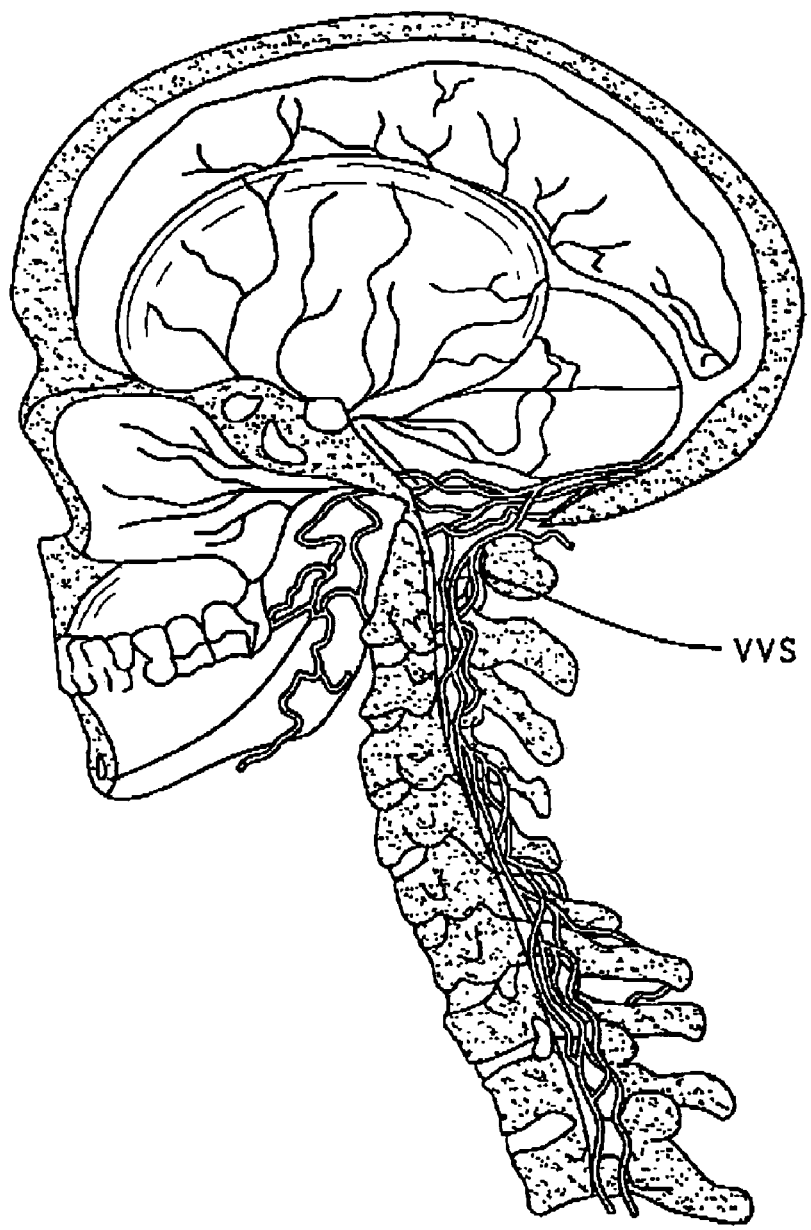
FIG. 1 is a scan of a photograph, taken at the National Library of Medicine, of plate 5 drawn by Breschet and published in 1828 (reference 56), depicting the cranial and vertebral venous systems, their anastomoses, and their anatomic characteristics, especially in relationship to other anatomic features of the brain and spine.

FIG. 1 depicts the anastomoses between the cranial and vertebral venous systems. Perispinal administration is preferably performed by a percutaneous injection into an interspinous space in the posterior cervical area (12 in FIG. 2). As shown in more detail in FIG. 2, needle 26 containing etanercept in solution is injected through the skin 18 into the interspinous space 24. If the needle penetrates the ligamentum flavum 22 then the etanercept will be injected into the epidural space 28 surrounding the spinal cord 36. Alternatively, an anatomic midline defect in the ligamentum flavum 22 allows the etanercept to more readily enter the epidural space 28. Etanercept acts to reduce the inflammation of neuronal tissue, either the brain or the inflamed nerve root 32 of this drawing.

The interspinous space 24 is defined as the space between two adjacent spinous processes 20. FIG. 3 shows the interspinous space 24 having veins 38 which collect the etanercept which reaches the interspinous space and drain said etanercept into the vertebral venous system, so that, utilizing the physical maneuvers of the present invention, the said etanercept is rapidly transported via retrograde blood flow to the brain. Alternatively, a catheter is implanted in either the interspinous space or the epidural space as another means of delivery of etanercept to the VVS.

DETAILED DESCRIPTION OF THE PREFERRED EMBODIMENTS

Perispinal administration is a novel new delivery method for etanercept for improving cognitive function.

For the purposes of this discussion, "perispinal" means in the anatomic vicinity of the spine, but outside of the intrathecal space. For this discussion "anatomic vicinity" is generally defined as within 10 centimeters, or functionally defined as in close enough anatomic proximity to allow the therapeutic molecules of consideration herein to reach the spine and/or the subarachnoid space surrounding the spinal cord in therapeutic concentration when administered directly to this area without necessitating direct intrathecal delivery. For the treatment of brain disorders, such as Alzheimer's, perispinal administration is effective because it delivers the biologic to the CNS in a therapeutic amount. The predominant method by which this is accomplished is through enhanced delivery of the therapeutic molecule to the brain via the vertebral venous system and/or to the brain via the cerebrospinal fluid. This occurs without direct intrathecal injection, but rather by direct transport utilizing a vascular route (the vertebral venous system) or by diffusion from the interspinous or epidural space into the subarachnoid space. This enhanced delivery of etanercept into the cerebrospinal fluid is facilitated by delivery of etanercept to the epidural space, either by direct placement, or by perispinal administration. Midline gaps in the ligamentum flavum will facilitate delivery of etanercept administered by midline percutaneous interspinous injection to the epidural space. Etanercept in the epidural space may then be delivered into the vertebral venous system, with subsequent delivery to the brain or into the cerebrospinal fluid. Excess TNF, at levels 25 times that of controls, has been documented in the CSF of patients with AD and MCI.

Perispinal administration of etanercept is accomplished by one of several preferred routes. The first is needle injection into the interspinous space. Etanercept is delivered to the interspinous space, in anatomic proximity to the ligamentum flavum, by midline interspinous needle injection. Midline defects in the ligamentum flavum are common, particularly in the cervical region. When present the midline ligamentum flavum defect provides a direct route of access for etanercept to the epidural space. Alternatively etanercept may be delivered directly into the epidural space by either direct epidural injection through the ligamentum flavum utilizing a syringe and needle; or by use of an indwelling catheter placed within the epidural space; or may be delivered into the epidural space by venous carriage via the subcutaneous veins and/or the external vertebral venous plexus. A catheter with a delivery lumen placed in the epidural or interspinous space can be connected to a pump, which may be placed remotely, such as in the abdominal area. Within the epidural space lies a richly interconnected vertebral (epidural) venous plexus, which is valveless and which is capable of transporting etanercept rapidly in the cephalad or caudad directions. This epidural venous plexus is directly connected to veins which perforate the ligamentum flavum and which drain the interspinous space; thus etanercept delivered into or adjacent to the interspinous space may drain into a communicating vein and thereby into the epidural venous plexus. Etanercept may thereby diffuse in both a caudad and cephalad direction via this venous network, and may therefore rapidly (within minutes) exert a widespread therapeutic effect on TNF-mediated processes which affect the nerve roots, dorsal root ganglia, and spinal cord at multiple spinal levels, or, of even greater relevance to this invention, the brain. Physical maneuvers are utilized to facilitate venous carriage of etanercept to the brain via the VVS. Additionally this epidural venous plexus is interconnected with the endoneurial vascular network, and etanercept thereby may gain access to the endoneurial space and the cerebrospinal fluid, crossing the dura utilizing this direct vascular access route. Additionally, once etanercept has gained access to the epidural space it may directly diffuse into the endoneurial space through the capsule of the dorsal root ganglion, which may present a less efficient barrier to macromolecules than the dural barrier of the spinal nerve roots.

Perispinal administration of etanercept is generally performed in a blind fashion, to deliver etanercept into either the interspinous space or the epidural space. Delivery of etanercept into the interspinous space results in subsequent delivery of etanercept into the vertebral venous system because the interspinous space is drained by subcutaneous veins and other veins which directly connect to the external vertebral venous plexus portion of the VVS. Etanercept delivered to the interspinous space also diffuses into the epidural space and into the CSF.

Placement of an indwelling catheter in the epidural or interspinous space is less technically difficult than placement within the subarachnoid space, and has additional advantages. For example the risk of infection is lower. And the risk of CSF fluid leak and resulting headache is lower.

Perispinal administration for delivery of neuroactive molecules other than etanercept, including biologics, cytokines, anti-cytokines, hormones or drugs via the vertebral venous system, in a manner similar to that outlined herein, may be performed. The neuroactive compounds include erythropoietin; GDNF; BDNF; NGF; human growth hormone; Kineret® (IL 1-RA); anti-IL-6; ABX-EGF and other compounds with CNS activity. Concurrent patent applications involving these other therapeutic molecules delivered through the CVVS are in development by the inventor.

Localized administration for the treatment of localized clinical disorders has many clinical advantages over the use of conventional systemic treatment. Locally administered medication after delivery diffuses through local capillary, venous, arterial, and lymphatic action to reach the anatomic site of pathology, or, alternatively, to reach the cerebrospinal fluid (CSF). In addition local administration of a biologic in the vicinity of the spine (perispinal administration) has the key advantage of improved delivery of the agent to the central nervous system (CNS), in most cases via the vertebral venous system (VVS) or via the CSF.

A specific anatomic route, by which etanercept delivered by perispinal administration reaches the brain, has been defined by the inventor. This route is as follows. Etanercept is delivered to the interspinous space in proximity to the ligamentum flavum by percutaneous injection through the skin by midline interspinous needle injection, or by way of an indwelling catheter whose distal lumen lies within the interspinous space. Etanercept delivered to the interspinous space (being the anatomic region in the midline of the back, in between two adjacent spinous processes) may directly enter the vascular system (predominantly venous) which drains the interspinous space and which veins communicate directly with the vertebral venous plexus. Alternatively etanercept delivered to the interspinous space may reach the epidural space via a defect in the ligamentum flavum. Midline defects in the ligamentum flavum are common, particularly in the cervical region. When present the midline ligamentum flavum defect provides a direct route of access for etanercept to the epidural space. Alternatively etanercept may be delivered directly into the epidural space by either direct epidural injection through the ligamentum flavum utilizing a syringe and needle; or by use of an indwelling catheter placed within the epidural space. Such catheter can be connected to a pump, which may be placed remotely, such as in the abdominal area. Within the epidural space lies a richly interconnected epidural venous plexus, which is valveless and which is capable of transporting etanercept rapidly in the cephalad or caudad directions (see Batson references 48 and 49). The epidural venous plexus communicates with the intracranial venous network and therefore provides direct access of biologics to the brain, via retrograde flow, which is facilitated by gravity when the patient is placed in certain positions. Specifically the epidural veins communicate with the basivertebral vein, the intracranial sigmoid, occipital, and basilar venous sinuses, and the azygous system (see references 44–50). Additionally the epidural venous plexus is interconnected with the endoneurial vascular network, and etanercept thereby may gain access to the endoneurial space and the cerebrospinal fluid, crossing the dura utilizing this direct vascular access route. Additionally, once etanercept has gained access to the epidural space it may directly diffuse into the endoneurial space through the capsule of the dorsal root ganglion, which may present a less efficient barrier to macromolecules than the dural barrier of the spinal nerve roots. TNF-alpha has been demonstrated to be 25 times elevated compared with normal controls in the cerebrospinal fluid in certain individuals with cognitive impairment and Alzheimer's Disease (see Tarkowski references 11 and 12). In the present invention, etanercept which reaches the cerebrospinal fluid will immediately bind (and inactivate) TNF circulating in the CSF and therefore immediately reduce its adverse biologic effects on the brain.

The inventor is using the vertebral venous system as a non-obvious route of administration for the inventions disclosed herein. For a venous system is routinely conceptualized as a system that drains blood from a target area or organ. For example the venous system which drains the kidneys is widely acknowledged to be a vascular system that drains blood from the kidneys, not as a way of delivering a therapeutic molecule to the kidneys. Likewise the venous system of the brain, which is normally recognized as the jugular venous system, is widely medically recognized as a system which functions to drain blood from, not to, the brain. The present invention is counter-intuitive as it uses the venous system to deliver a therapeutic molecule to the brain. Likewise the use of the vertebral venous system (which the inventor proposes is a misnomer, and alternatively suggests should be designated as the cranio-vertebral venous system) to achieve delivery of therapeutic compounds to the brain, spinal cord, dorsal root ganglion, or nerve roots is not obvious, because conventional thinking is that this venous system functions to drain venous blood away from these anatomic sites. Therefore the inventions disclosed here are in this way counter-intuitive, because they rely on the cranio-vertebral venous system to deliver therapeutic molecules (including specifically etanercept) to the brain, brainstem, meninges, spinal cord, dorsal root ganglion, and nerve roots. This delivery is accomplished by inducing retrograde venous flow (the opposite direction from the usual direction), which is made possible by the lack of valves in this venous system, and by the proper use of gravity and positioning of the patient so that venous flow in the retrograde direction is accomplished. The rich connections between the cranial venous system and the vertebral venous system was beautifully depicted in 1828 by Breschet (reference 56), and a detailed discussion of this interconnection was made by Batson in 1940 and thereafter. The inventor has found a single intact copy of the Breschet plates, which are life-size and hand colored, in the special collections of the National Library of Medicine and has arranged for these to be photographed. A copy of plate 5 from this collection is included as an exhibit for this patent (FIG. 1), and illustrates the anatomical connection between the cranial and vertebral venous systems, an anatomic route which remains largely unrecognized by the medical community despite its careful depiction more than a century and a half ago.

The vertebral venous system is continuous along the length of the spine, but is, of course, closest to the brain in the cervical (neck) region. The vertebral venous plexus is extensive in the cervical region, and in this area defects in the ligamentum flavum are also more common, both of which factors help etanercept delivered to the cervical interspinous space to reach the brain. For all of these reasons, for this invention the usual point of injection for perispinal etanercept is in the posterior neck, overlying the spine. (As an alternative, perispinal administration of etanercept into the interspinous space can also be performed in the lumbar or thoracic regions since the vertebral venous system is continuous).

Correct positioning of the patient so as to facilitate retrograde blood flow in the cranial direction is utilized as part of the present invention to achieve improved delivery of etanercept to the brain. After a posterior cervical interspinous injection of etanercept in sterile water the patient is rapidly placed in the prone position and then the plane of the examining table is placed head-downward (Trendelenburg)

to facilitate retrograde delivery to the brain and the cranial venous system. Etanercept, because of its biologic nature, is uniquely suited to delivery via the CVVS to the brain, because of its nearly instantaneous therapeutic effect. This instantaneous effect is the direct consequence of the fact that etanercept, in contradistinction to synthetic drugs which are not of biologic origin, does not function by influencing intermediary processes, but rather binds directly to soluble TNF. Therefore prolonged bathing of the target tissue by the therapeutic molecule is not necessary. Excess TNF is thereby rapidly bound and its adverse physiologic effects are immediately interdicted, including its adverse effects upon cognition.

The cranio-vertebral venous system is both anatomically and physiologically distinct from the venous system which drains the abdomen and thorax, which has been designated by others as the intracavitary venous system, with the cranio-vertebral venous system designated as the extracavitary venous system. Other nomenclature for the CVVS also comes to mind, such as the valveless venous system, or the bi-directional venous system, but they are perhaps less suitable than the CVVS. CVVS, of course, neglects to include the pelvic venous system, to which the CVVS is caudally connected, which would make the proper designation the CVPVS; but for purposes of this patent the inventor chooses to use the CVVS or VVS to emphasize the aspects of this invention which are deserving of the most attention. The CVVS and the intracavitary venous system do share anastomoses, as has been discussed at length by Batson. Batson has also described the retrograde flow possible with the VVS, but has not proposed the possible use of the VVS as a route to deliver therapeutic compounds to the brain, nor has anyone else. Again, this retrograde route of delivery is uniquely possible utilizing the VVS because of the lack of venous valves. In the present invention the CVVS is especially important for the rapid transport of etanercept to the brain of the human with changes in posture.

Placement of an indwelling catheter in the epidural space, or, alternatively, in the interspinous space, is less technically difficult than placement within the subarachnoid space, and has additional advantages. For example the risk of infection is lower. And the risk of CSF fluid leak and resulting headache is lower or nonexistent. The methods of the present invention are therefore distinguished from direct intrathecal administration of etanercept.

Etanercept has many biologic effects. Etanercept, for example, in addition to being a potent anti-inflammatory also has important anti-apoptotic effects which may be of particular importance in treating neurodegenerative diseases, such as Alzheimer's Disease, where apoptosis plays a pathogenetic role.

Biologics have been developed which have been shown to offer dramatic clinical benefit for systemic illnesses in humans, even for those disorders which have not responded to large and repeated doses of corticosteroids. These biologics fall into the category of cytokine antagonists because they block, or antagonize, the biologic action of a specific cytokine which has adverse clinical effects. For the purposes of this discussion, "antagonist", "inhibitor", and "blocker" are used interchangeably.

Perispinal delivery can also be used to deliver other types of therapeutic agents to the brain, cerebrospinal fluid, spine, or spinal cord. These therapeutic agents include pharmacologic agents or other cytokine antagonists. Perispinal delivery, however, is particularly advantageous when biologics, such as etanercept, are administered because of their efficacy at extremely low concentration (high biologic potency).

A detailed example of perispinal administration of etanercept utilizing an indwelling epidural catheter follows: An indwelling sterile catheter whose distal lumen lies within the epidural space is surgically implanted in a human with Alzheimer's Disease. During the surgical procedure the proximal end of the catheter is attached to a battery-powered pump which contains a reservoir containing 10 ml of etanercept in sterile water (10 mg/ml). The pump is surgically implanted in the abdomen during the same procedure in which the epidural catheter is implanted. The reservoir pump is positioned in the subcutaneous space with orientation and placement such that the reservoir is accessible to replenishment by percutaneous injection. The etanercept solution may be replenished by percutaneous injection periodically, because the reservoir has a port covered by a material, such as latex or a similar material which is penetrable by needle injection but which will self-seal once the needle is withdrawn. The pump is set to deliver etanercept at a rate of 20 mg per week. Therefore it will need to be refilled once every five weeks. The patient returns to the physician's office once every five weeks for the etanercept solution to be refilled by percutaneous instillation of etanercept solution.

One of the advantages of perispinal delivery into the interspinous space is that administration is simplified. This route is simple and safe. Hemorrhage due to the use of long or large bore needles is minimized because perispinal administration, by the subcutaneous route, requires only a short, narrow bore needle. Time-consuming and difficult epidural injection is not necessary. Epidural needle injection, for the purposes of this patent, is also a form of perispinal administration, and, in certain clinical circumstances may be the delivery method of choice, despite its greater difficulty and greater risk.

Epidural needle injection may be accomplished by percutaneous introduction of the needle carried through an intact ligamentum flavum to reach the epidural space. Gaps in the ligamentum flavum, including recently disclosed midline gaps, facilitate epidural delivery of etanercept to the epidural space after more superficial interspinous perispinal delivery. Local perispinal administration also has the advantage of providing a depot of therapeutic medication in the surrounding tissue, which will provide therapeutic levels of medication to the treatment site for a prolonged period of time. This decreases the necessity for another injection of medication. Additionally, administering medication locally limits the exposure of the medication to the systemic circulation, thereby decreasing renal and hepatic elimination of the medication, and decreasing exposure of the medication to systemic metabolism. All of these factors tend to increase the therapeutic half-life of the administered cytokine antagonist. Taken together, all of these forms of localized anatomic administration have significant clinical advantages over the various forms of systemic administration customarily used to deliver etanercept. The usual and customary route of administration for etanercept is systemically, by subcutaneous administration in the abdomen, thigh, or forearm. Intravenous administration of etanercept is another systemic route, as is intramuscular etanercept when etanercept is given at a site remote from the spine, such as the deltoid or gluteal region.

For the sake of this invention, the following definitions also apply: perilesional is defined as in anatomic proximity to the site of the pathologic process being treated; and peridural is defined as in anatomic proximity to the dura of the spinal cord, but specifically excluding intrathecal injection. The "interspinous route" for the purposes of this patent, is defined as parenteral injection through the skin in or near the midline, in the interspace between two spinous processes, to deliver etanercept in anatomic proximity to the epidural space and the vertebral venous plexus.

For the sake of this invention "on a chronic basis" means for a period exceeding two months.

EXPERIMENTAL RESULTS

An IRB-approved clinical trial utilizing perispinal etanercept was begun by the inventor in 2004 and clinical data is available, although the clinical trial is ongoing. A summary of the study follows:
- A. Eligibility: All subjects admitted to study had been previously diagnosed by a board-certified neurologist with either Mild Cognitive Impairment, possible Alzheimer's Disease (AD), or probable AD (meeting NINCDS-ADRDA Criteria) and must be between 65 and 85 years of age. All subjects had MRI or CT Scan results consistent with AD or MCI.
- B. Exclusions: Any subject under the age of 65 or over the age of 85 with multiple sclerosis (or any other demyelinating disorders), abnormal white blood cell counts, anemia, pregnancy, diabetes mellitus, history of tuberculosis, history of lymphoma, bleeding disorders, or active infection at the time of treatment will not be allowed admission into the study. Female subjects who are not menopausal, sterile, or are not on acceptable birth control will be excluded. Additional exclusionary criteria are the following:
  1. Use of another investigational agent within 1 month of the screening visit.
  2. History of clinically significant stroke.
  3. Current evidence or history in the past 2 years of seizures, head injury with loss of consciousness and/or immediate confusion after the injury.
  4. History of any major psychiatric disorder including psychosis, major depression, schizophrenia, bipolar disorder, alcohol or substance abuse.
  5. Absence of a reliable caregiver.
  6. Clinical or radiological evidence for other neurological disorders such as Parkinson's disease, normal pressure hydrocephalus, multi-infarct dementia, idiopathic seizure disorder, CNS infectious disease.
  7. Platelet count<100,000.
  8. History of positive PPD and/or tuberculosis.
  9. MMSE<20.
  10. Modified Hachinski score>4, indicating probable vascular component to dementia.

Study Design: Admitted subjects were given extensive cognitive testing prior to treatment to establish their neurocognitive baseline, utilizing several or all of the following tests: Mini-Mental Status Exam (MMSE); Alzheimer's Disease Assessment Scale—Cognitive Subscale (ADAS-Cog/11)[2] to assess general cognitive status; Comprehensive Trail-Making Test (CTMT)[3] to assess frontal lobe deficit through visual search and sequencing tasks; Boston Naming Test (BNT)[4] to assess dysnomia (difficulty in recalling or remembering names and/or words) by measuring subject's ability to name objects; California Verbal Learning Test-$2^{nd}$ Edition (CVLT-2)[5] to assess the subject's word recall and recognition skills; Wechsler Memory Scale-$3^{rd}$ Edition Abbreviated (WMS-III abbreviated)[6] to test an assortment of specific memory deficits (auditory immediate, visual immediate, memory immediate, auditory delayed, visual delayed, auditory recognition delayed, general memory and working memory); Categories test (FAS)[7] to assess subject's word finding skills; University of Pennsylvania Smell Identification Test (UPSIT)[8] to assess olfactory (smell) deficit, as smell loss has been found to be a presenting symptom in patients with MCI and AD and is associated with early significant disease presence in the areas of the brain thought to mediate olfactory function[9]; and Beck Depression Inventory (BDI)[10] to assess subject's level of depression, as depression is common in both MCI and AD. Subjects were instructed to continue their previous medications without change during the duration of the study. Subjects were given a single dose of perispinal etanercept 25 mg weekly for 5 consecutive doses, administered by subcutaneous injection to the interspinous space in the midline in the lower cervical region, usually between C5 and C7. Administration was performed with the subject in the sitting position, with the head bent forward. Immediately thereafter the patient was placed in the prone position, in a modified Trendelenburg position with the head directed downward about 15 degrees. This position was maintained for five to ten minutes, and then the patient was slowly allowed to resume the standing position. Cognitive testing was performed at intervals following treatment, including one month following treatment, utilizing one or more of the neurocognitive tests outlined supra. Quantitated caregiver reports were obtained at baseline and then weekly following treatment. Subjects were given the option of continuing treatment for 6 months following enrollment.

Results: Three subjects have been enrolled at the present time. Each had deficits of −11, −7, and −22 on ADAS-Cog/11 at baseline. All subjects and their caregivers reported significant clinical improvement following the first dose of perispinal etanercept, with improvement in memory, personality, and ability to accomplish the daily tasks of living more easily, with improvement persisting throughout the duration of the study. Clinical improvement was confirmed by neurocognitive testing, including improvement noted on the letter portion of the FAS; improvement noted on the immediate free recall subset of the CVLT; and improvement in Trails performance, all as measured compared with baseline at approximately one month after study initiation (four weekly doses, measurement approximately 6 days after the fourth dose) utilizing perispinal etanercept delivered as noted above. Subject 3 had both behavioral improvement and improvement on ADAS-Cog/11 (from −22 to −17) documented at 7 days following the fourth dose of perispinal etanercept. In addition notable and significant improvement in behavior were noted by all three subjects and their caregivers. The investigator noted rapid improvement in cognitive function in all three individuals following perispinal etanercept. Behavioral improvement was especially noticeable to each of the caregivers following the first perispinal etanercept dose. Caregivers for each of the three study subjects noticed a tendency for greater improvement during the first few days after each dose. One study subject was aware of this tendency himself, and advised the principal investigator (the inventor) that he was aware that his memory function began to deteriorate somewhat beginning several days after each dose of perispinal etanercept. No adverse effects of treatment were noted. One subject developed a mild upper respiratory infection during the first month of treatment.

The physical maneuvers outlined above enhance the delivery of etanercept to the brain via the VVS. When standing, with the head in the upright position, venous efflux from the brain via the VVS is augmented. When the head is bent over in the sitting position venous efflux from the brain via the VVS is diminished, with the majority of the venous efflux occurring through the jugular venous system. Immediately after the injection the patient is placed in the prone position. The prone position increases intra-abdominal pressure, thereby increasing flow in the VVS in the cephalad direction, and also aids in the venous drainage from the interspinous space into the VVS, which is located anterior to the interspinous space, and which is therefore below the site of injection when the patient is in the prone position. After prone placement, the plane of the examining table is then directed so that the patient's head is directed downward. The patient is therefore placed in a modified Trendelenburg position, with the head downward, and the etanercept solution, which has been injected into the interspinous space drains via subcutaneous and other veins into the external vertebral venous system, which then drains into the internal vertebral venous system, which then drains, because of the hydrodynamics induced by this physical position and gravity, in a retrograde fashion, from the VVS into the cranial veins and thereby is delivered, retrograde, to the brain itself. Some patients are additionally positioned so that their head is directly entirely downward by draping their head over the side of the table. Additionally etanercept carried by the VVS can reach the jugular venous system through venovenous anastomoses, and can reach the brain through retrograde flow through the jugular venous system, although this is more difficult and less efficient that retrograde flow directly from the VVS into the cranial venous system. In this manner the etanercept bypasses the blood-brain barrier which is in place on the arterial side of the brain. The venous system of the brain normally functions to facilitate exit of blood and dissolved molecules from the brain in an efficient manner. Therefore it does not contain the efficient "filters" (the blood-brain barrier) that are necessary to protect the brain from molecules which are delivered by the normal supply route, the brain's arterial-capillary system.

These physical maneuvers, designed to augment venous carriage of etanercept delivered by perispinal administration to the brain, have not been previously described. These physical maneuvers also result in increased delivery of etanercept via CSF carriage into the brain, and likewise have not been previously described as a method to deliver etanercept to the brain.

This invention is distinguished from the prior art in a variety of ways, including the use and description of novel and useful new uses, methods of use, and concepts involving TNF binding biologics, including:

1. Novel uses of TNF binding biologics to improve cognitive impairment or produce cognitive enhancement;
2. Perispinal (extrathecal) administration distinguished from systemic forms of administration and intrathecal administration;
3. The use of non-monoclonal antibody anti-TNF biologics as distinguished from the use of monoclonal antibody TNF biologics;
4. Intranasal administration of TNF binding biologics as a method of delivery to the CNS;
5. The use of TNF binding biologics to reduce cognitive impairment;
6. The use of TNF binding biologics for cognitive inhancement;
7. The use of the vertebral venous system to deliver therapeutic molecules to the brain;
8. The use of physical maneuvers to facilitate delivery of therapeutic molecules to the brain;
9. The use of physical maneuvers to influence the direction of venous flow within the cranio-vertebral venous system and thereby deliver therapeutic molecules to the site of neuronal inflammation;
10. The use of retrograde venous perfusion to deliver therapeutic molecules to the brain, dorsal root ganglion, nerve roots, and spinal cord;
11. The use of retrograde venous perfusion via the cranio-vertebral venous system to allow therapeutic molecules to bypass the blood-brain barrier and therefore reach the brain;
12. The use of defects in the ligamentum flavum to facilitate delivery of perispinally administered etanercept to reach the epidural space;
13. The use of the cranio-vertebral venous system as a "back door" to facilitate delivery of therapeutic molecules to the brain, brainstem, meninges, spinal cord, dorsal root ganglion, and nerve roots;
14. The use of perispinal administration to introduce etanercept into the vertebral venous system;
15. The use of perispinal administration to introduce etanercept into the cerebrospinal fluid;
16. The use of etanercept, a dimeric fusion protein, as distinguished from a simple soluble TNF receptor, to produce prolonged improvement in cognitive function;
17. The use of etanercept delivered by perispinal administration to produce cognitive improvement or to slow disease progression in certain neurological disorders characterized by progressive dementia and TNF-mediated brain inflammation (such as Alzheimer's Disease);
18. The use of etanercept delivered by intranasal administration as a method to enable it to cross the blood-brain barrier and thereby be used to improve cognitive function.

PREFERRED EMBODIMENTS

In one preferred embodiment a patient with Alzheimer's Disease with dementia is treated by injection of etanercept, in a therapeutically effective dose to the perispinal area, with the dose repeated as a form of chronic therapy at intervals as often as twice per week to as little as once per three months.

In another preferred embodiment a patient with AIDS dementia is treated by injection of etanercept, in a therapeutically effective dose to the perispinal area, with the dose repeated as a form of chronic therapy at intervals as often as twice per week to as little as once per three months.

In another preferred embodiment a patient with Alzheimer's Disease is treated by injection of Enbrel®, using a 25 mg dose mixed with the sterile water solution supplied by the manufacturer (which contains benzyl alcohol), to the anatomic area adjacent to the spine, with the dose repeated as a form of chronic therapy at intervals as often as twice per week to as little as once per three months.

In another preferred embodiment a patient with cognitive impairment is treated by a perispinal injection of Enbrel®, using a 25 mg dose in solution, delivered by midline transcutaneous injection overlying the spine in the lower posterior neck area, with the patient sitting and head flexed forward, with immediate placement of the patient in the prone position with the plane of the examination table directed head downward about 15 degrees after the injection, and maintenance of the patient in this modified Trendelenburg prone position for several minutes after injection, with the dose repeated as a form of chronic therapy at intervals as often as twice per week to as little as once per three months.

In another preferred embodiment an individual without cognitive impairment, who desires to achieve enhanced cognitive function, is treated by a perispinal injection of Enbrel®, using a 25 mg dose in solution, delivered by midline transcutaneous injection overlying the spine in the lower posterior neck area, with the patient sitting and head flexed forward, with immediate placement of the patient in the prone position with the plane of the examination table directed head downward about 15 degrees after the injection, and maintenance of the patient in this modified Trendelenburg prone position for several minutes after injection, as either a single dose, or with doses repeated as often as once per week.

In another preferred embodiment a patient with Alzheimer's Disease is treated by administration of etanercept into the epidural space utilizing an indwelling epidural catheter on a chronic basis.

In another preferred embodiment a patient with cerebrovascular disease is treated by administration of etanercept into the epidural space utilizing an indwelling epidural catheter on a chronic basis.

In another preferred embodiment a patient with Minimal Cognitive Impairment is treated by administration of etanercept into the epidural space utilizing an indwelling epidural catheter on a chronic basis.

In another preferred embodiment a patient with Alzheimer's Disease is treated by administration of etanercept into the epidural space utilizing an indwelling epidural catheter connected to a remotely placed pump which contains a reservoir of etanercept in solution.

In another preferred embodiment a patient with Mild Cognitive Impairment is treated by administration of etanercept into the epidural space utilizing an indwelling epidural catheter connected to a remotely placed pump which contains a reservoir of etanercept in solution.

In another preferred embodiment a patient with cognitive impairment is treated by administration of etanercept into the interspinous space utilizing an indwelling interspinous catheter connected to a remotely placed pump which contains a reservoir of etanercept in solution.

In another preferred embodiment a patient with cognitive impairment is treated by administration of etanercept delivered into the epidural space on either a continuous or intermittent basis so that a total of from 1 mg to 50 mg of etanercept per week is given.

In another preferred embodiment a patient with cognitive impairment is treated by administration of etanercept delivered into the epidural space on either a continuous or intermittent basis so that a total of from 50 mg to 2500 mg of etanercept is given per year.

In another preferred embodiment a patient with cognitive impairment is treated by administration of etanercept delivered into the epidural space on either a continuous or intermittent basis so that a total of approximately 1000 mg of etanercept is delivered per year.

In another preferred embodiment a patient with cognitive impairment is treated by administration of etanercept delivered into the epidural space utilizing an indwelling epidural catheter connected to a remote pump which is implanted in the abdominal area which contains a reservoir of etanercept in solution, and which is designed so as to deliver a weekly dose of 20 mg of etanercept into the epidural space.

In another preferred embodiment a patient with Mild Cognitive Impairment is treated by administration of etanercept delivered into the epidural space utilizing an indwelling epidural catheter connected to a remote pump which is implanted in the abdominal area which contains a reservoir of etanercept in solution, and which is designed so as to deliver a weekly dose of 5–20 mg of etanercept into the epidural space.

In another preferred embodiment a patient with Alzheimer's Disease is treated by administration of etanercept delivered into the epidural space utilizing an indwelling epidural catheter connected to a remote pump which is implanted in the abdominal area which contains a reservoir of etanercept in solution, and which is designed so as to deliver a weekly dose of 5–20 mg of etanercept into the epidural space.

In another preferred embodiment a patient with dementia is treated by administration of etanercept delivered into the epidural space utilizing an indwelling epidural catheter connected to a remote pump which is implanted in the abdominal area which contains a reservoir of etanercept in solution, and which is designed so as to deliver a weekly dose of 5–20 mg of etanercept into the epidural space.

In another preferred embodiment a patient with cognitive impairment is treated by administration of etanercept delivered into the interspinous space utilizing an indwelling interspinous catheter connected to a remote pump which is implanted in the abdominal area which contains a reservoir of etanercept in solution, and which is designed so as to deliver a weekly dose of 10 mg to 50 mg of etanercept into the interspinous space.

In another preferred embodiment a patient with Alzheimer's Disease is treated by a perispinal injection of etanercept utilizing the midline interspinous route, using the 25 mg dose in the vial as supplied by the manufacturer as part of the Enbrel® package, but instilling, into the vial containing etanercept, 1 ml of plain sterile water, which does not contain benzyl alcohol, and using this plain sterile water as the mixing agent for the etanercept. The dose is then repeated as a form of chronic therapy at intervals as often as twice per week to as little as once per three months.

In another preferred embodiment a patient with Alzheimer's Disease is treated by injection of etanercept, using a dose varying between 5 mg and 50 mg of etanercept, mixed with 0.5 to 5 ml of sterile water without the addition of a preservative, to the perispinal area, with the dose repeated as a form of chronic therapy at intervals as often as twice per week to as little as once per three months.

In another preferred embodiment a patient with Mild Cognitive Impairment is treated by injection of etanercept, using a dose varying between 5 mg and 50 mg of etanercept, mixed with 0.5 to 5 ml of sterile water without the addition of a preservative, to the perispinal area, with the dose repeated as a form of chronic therapy at intervals as often as twice per week to as little as once per three months.

In another preferred embodiment a patient with dementia of unknown cause is treated by injection of etanercept, using a dose varying between 5 mg and 50 mg of etanercept, mixed with 0.5 to 5 ml of sterile water without the addition of a preservative, to the perispinal area, with the dose repeated as a form of chronic therapy at intervals as often as twice per week to as little as once per three months.

In another preferred embodiment a human with mild cognitive impairment, thought to be the early stage of Alzheimer's disease, is treated by injection of etanercept, using a dose of 25 mg of etanercept mixed with 1 ml of sterile water, to the perispinal area by midline interspinous injection, utilizing a 1.5 cm needle in the cervical region, just superior to the C6 spinous process, at a depth of 1.2 cm, with the dose repeated as a form of chronic therapy at an interval of once per week.

In another preferred embodiment a human with mild cognitive impairment, thought to be the early stage of Alzheimer's disease, is treated by injection of Enbrel®, to the perispinal area by midline interspinous injection, utilizing a 1.5 cm needle in the cervical region, just superior to the C6 spinous process, at a depth of 1.2 cm, with the dose repeated as a form of chronic therapy at an interval of once per week.

In another preferred embodiment a human with dementia is treated by injection of Enbrel®, to the perispinal area by midline interspinous injection, with the dose repeated as a form of chronic therapy at an interval varying between two to thirty days between doses.

In another preferred embodiment injection of the therapeutic molecule to the perispinal area is accomplished by percutaneous injection into the anatomic area between two adjacent spinous processes ("the interspinous space").

In another preferred embodiment interspinous injection is accomplished by injection through the skin.

Scientific Background:

Antibodies (immunoglobulins) are proteins produced by one class of lymphocytes (B cells) in response to specific exogenous foreign molecules (antigens). Monoclonal antibodies (mAB), identical immunoglobulin copies which recognize a single antigen, are derived from clones (identical copies) of a single B cell. This technology enables large quantities of an immunoglobulin with a specific target to be mass produced.

Monoclonal antibodies with a high affinity for a specific cytokine will tend to reduce the biologic activity of that cytokine. Substances which reduce the biologic effect of a cytokine can be described in any of the following ways: as a cytokine blocker; as a cytokine inhibitor; or as a cytokine antagonist. In this patent, the terms blocker, inhibitor, and antagonist are used interchangeably with respect to cytokines.

Advances in biotechnology have resulted in improved molecules as compared to simply using monoclonal antibodies. One such molecule is CDP 870 which, rather than being a monoclonal antibody, is a new type of molecule, that being an antibody fragment. By removing part of the antibody structure, the function of this molecule is changed so that it acts differently in the human body. Another new type of molecule, distinct from monoclonal antibodies and soluble receptors, is a fusion protein. One such example is etanercept. This molecule has a distinct function which acts differently in the human body than a simple soluble receptor or receptors.

Monoclonal antibodies, fusion proteins, and all of the specific molecules discussed above under the categories of TNF antagonists and interleukin antagonists are considered biologics, in contrast to drugs that are chemically synthesized. For the purpose of this patent a biologic is defined as a molecule produced through recombinant DNA technology which is derived from the DNA of a living source. The living sources may include humans, other animals, or microorganisms. The biologics mentioned above are manufactured using biotechnology, which usually involves the use of recombinant DNA technology. Cytokine antagonists are one type of biologic. Biologics are regulated through a specific division of the FDA.

Cytokine antagonists can take several forms. They may be monoclonal antibodies (defined above). They may be a monoclonal antibody fragment. They may take the form of a soluble receptor to that cytokine. Soluble receptors freely circulate in the body. When they encounter their target cytokine they bind to it, effectively inactivating the cytokine, since the cytokine is then no longer able to bind with its biologic target in the body. An even more potent antagonist consists of two soluble receptors fused together to a specific portion of an immunoglobulin molecule (Fc fragment). This produces a dimer composed of two soluble receptors which have a high affinity for the target, and a prolonged half-life. This new molecule is called a fusion protein. An example of this new type of molecule, called a fusion protein, is etanercept (Enbrel®).

TNF, a naturally occurring cytokine present in humans and other mammals, plays a key role in the inflammatory response, in the immune response and in the response to infection. TNF is formed by the cleavage of a precursor transmembrane protein, forming soluble molecules which aggregate in vivo to form trimolecular complexes. These complexes then bind to receptors found on a variety of cells. Binding produces an array of pro-inflammatory effects, including release of other pro-inflammatory cytokines, including IL-6, IL-8, and IL-1; release of matrix metalloproteinases; and up regulation of the expression of endothelial adhesion molecules, further amplifying the inflammatory and immune cascade by attracting leukocytes into extravascular tissues.

Etanercept (Enbrel®, Amgen), infliximab (Remicade®), adalimumab, CDP 870, and onercept are potent and selective inhibitors of TNF. CDP 870 and onercept are in clinical development. Etanercept, adalimumab, and infliximab are FDA approved for chronic systemic use to treat rheumatoid arthritis and certain other chronic inflammatory disorders.

Clinical Disorders

Patients with the following clinical disorders, among others, will benefit from treatment with cytokine antagonists delivered by the perispinal route:

1. Dementing Disorders. These conditions include dementia or cognitive impairment suspected or established as due to Alzheimer-type pathology, including Mild Cognitive Impairment (MCI), Possible Alzheimer's Disease, Probable Alzheimer's Disease, Alzheimer's Disease, and Senile Dementia/Alzheimer's type; Idiopathic Dementia or Dementia of unknown cause; Dementia with Lewy Bodies, also called Diffuse Lewy Body Disease; Picks Disease and other forms of frontotemporal dementia; and Vascular Dementia. Excess levels of TNF have been detected in the CSF of patients with AD and MCI, and have been implicated in the pathogenesis of other forms of dementia, TBI, and neuronal inflammation. The pathogenesis of these disorders may involve CNS and neuronal inflammation, and many also involve accelerated neuronal apoptosis. Treatment of these disorders with perispinal etanercept leads to cognitive improvement and/or slowing of disease progression. Chronic treatment regimens are necessary utilizing perispinal etanercept.

2. Mild Cognitive Impairment. Mild cognitive impairment (MCI), for the purposes of this invention, is considered to be the condition of cognitive impairment resulting in memory difficulties in a human for which a secondary cause (such as stroke, drug toxicity, infection, etc.) has not been established. Alternatively mild cognitive impairment may be considered to be present in an adult not meeting the clinical criteria for dementia or AD but still deemed to be cognitively impaired for which a treatable etiology has not been uncovered. These individuals are considered to have a high risk of progressing to dementia or AD. Excess levels of TNF have been detected in the CSF of patients with MCI and have been associated with an increased risk of progression from MCI to AD. There are no curative treatment regimens currently available. The pathogenesis of MCI involves CNS and neuronal inflammation, and many also involve accelerated neuronal apoptosis. Treatment of individuals with MCI with etanercept leads to clinical improvement and/or slowing of disease progression or slowing of progression to dementia or AD. Chronic treatment regimens are necessary utilizing perispinal etanercept, usually on a continuing weekly dosage basis.

3. Cerebrovascular Disease. Patients with cerebrovascular disease may have cognitive dysfunction, which may be exacerbated by TNF-mediated neuronal inflammation. TNF has been shown to increase neuronal damage in experimental settings studying the effect of vascular occlusion. Additionally progression of cerebrovascular disease may occur through intimal and other forms of vascular inflammation which are at least in part mediated through TNF. Inhibition of TNF utilizing perispinal etanercept will therefore have a direct beneficial effect through inhibition of both vascular and neuronal inflammation. Chronic treatment with perispinal etanercept is necessary.

4. Traumatic Brain Injury and other forms of non-infectious and non-malignant Cognitive Impairment. Cognitive impairment (CI), for the purposes of this invention, is considered to be the condition of cognitive impairment resulting in memory difficulties or other difficulties in cognition in a human which cannot be adequately treated with existing medical modalities, and which is not caused by an infection or by a brain tumor, either primary or metastatic. Many patients with CI and TBI may be experiencing CNS and neuronal inflammation mediated by TNF. Treatment of individuals with TBI or these forms of CI utilizing perispinal etanercept leads to clinical improvement and/or slowing of disease progression or slowing of progression to advanced dementia. Chronic treatment regimens are necessary utilizing perispinal etanercept.

5. Cognitive Enhancement utilizing perispinal etanercept for humans without demonstrable brain pathology. A wide variety of methods are utilized by the general population to improve cognitive performance, ranging from a simple cup of coffee in the morning, to the use of caffeine lozenges, *ginkgo biloba*, amphetamines and other pharmaceuticals. For certain of these individuals optimum or improved cognitive performance at times may be of critical importance. Examples might include test-taking; a important public debate; combat or other such situations. Other individuals may note cyclical changes in cognitive performance. Such individuals, all without brain pathology, might wish to occasionally augment their usual cognitive performance. TNF levels in the brain are known to be altered with sleep-wake cycles and may otherwise vary with normal activity. Down modulation of brain and CSF TNF, utilizing intermittent perispinal etanercept, will result in improved cognitive function, even in individuals with TNF levels considered to be within the normal range. Perispinal etanercept does not result in elimination of all TNF; this result would not be desirable, because a certain amount of TNF is necessary for normal brain functioning. The individuals in this category therefore fall into two groups: first, individuals without brain pathology but with cyclical normal diminution in cognitive performance who wish to enhance their cognitive function; and second, individuals who simply wish to enhance their undiminished cognitive ability. Perispinal etanercept delivered as a single dose to the posterior cervical area, usually at a dose of 25 to 50 mg administered into the interspinous space between C5 and C7, rapidly followed by placement of the patient in a head down position for several minutes, is the method used for these individuals.

6. Cognitive Impairment in individuals with excess TNF production due to a rheumatologic disorder or psoriasis. The disorders of consideration here include specifically rheumatoid arthritis, psoriatic arthritis, psoriasis, juvenile rheumatoid arthritis, and ankylosing spondylitis which are each associated with excess TNF production. Rheumatoid arthritis in both children and adults is a well-recognized autoimmune type of arthritis whose initial cause is unknown. Psoriatic arthritis is a seronegative spondyloarthropathy which is well recognized. Psoriasis is a well known chronic inflammatory disorder of the skin characterized by persistent, chronic, plaques in one of several characteristic patterns. Ankylosing spondylitis is a chronic, autoimmune inflammatory disorder of the spine. All of these diseases have been shown to involve excess TNF. Etanercept, delivered systemically by either subcutaneous or intravenous (intracavitary) administration at sites remote from the spine has been demonstrated in to result in clinical improvement, and etanercept is FDA-approved for treating each of these conditions. However etanercept delivered by perispinal administration has not previously been suggested as a treatment for any of these conditions, and specifically has not previously been suggested as a treatment to improve or prevent cognitive impairment associated with these clinical disorders. The present invention involves the perispinal administration of etanercept to deliver etanercept into the VVS, and thereby into the brain via retrograde delivery via the cranial venous connections to the VVS. This is a method of delivering etanercept into the extracavitary venous system, and thereby to deliver etanercept to the brain via this "back door". By so doing the cognitive impairment which accompanies these disorders, and which has not been previously recognized as such (instead attributed to fatigue and chronic pain), is ameliorated. Perispinal etanercept can be combined with systemic delivery of etanercept. For example, a patient with rheumatoid arthritis and cognitive impairment may receive a single dose of perispinal etanercept per month as a replacement for a dose of subcutaneous etanercept which would have been administered in the abdomen. Chronic dosing regimens are necessary because of continued excess TNF production in these disorders.

7. Cognitive impairment in individuals with cancer cachexia and cancer metastatic to bone. These conditions are known to be associated with excess TNF. The inventor has previously demonstrated improvement in both of these conditions as a result of perispinal etanercept (see Tobinick reference 13). Many different forms of cancer elaborate TNF. For these cancers TNF is a growth factor (see Tobinick reference 13), rather than an anti-cancer agent, as previously thought. Excess TNF reaches the extracavitary venous system via anastomoses from the intracavitary venous system, and thereby reaches the brain. These patients thereby benefit from perispinal administration of etanercept, which leads to cognitive improvement. Dosing requirements vary, ranging from one or two doses to chronic intermittent dosing.

8. Cognitive impairment in individuals with chronic back pain. The inventor has previously demonstrated clinical improvement in patients with chronic back pain due intervertebral disc disease and associated conditions, through the use of perispinal etanercept (see Tobinick references 14, 15, and 16). Annular tear of the intervertebral disc, disc protrusion, and associated conditions have been shown to result in the elaboration of TNF resulting in chronic pain (references 14, 15, 16). Recently, decreased brain size has been found to be associated with chronic back pain (reference 57). The inventor's work provides an explanation for this association: chronic back pain is associated with increased TNF production, which finds its way into the VVS and thereby into the brain, where it produces neuronal damage, cognitive impairment, and brain shrinkage. These patients thereby benefit from perispinal administration of etanercept, which leads to cognitive improvement. Initial dosing is usually two doses of etanercept 25 mg delivered by perispinal etanercept separated by an interval of one week, with additional doses administered as necessary to achieve control of pain. Some patients require monthly dosing.

9. AIDS Dementia. AIDS (HIV) Dementia is a well known complication of chronic infection with the human immunodeficiency virus. TNF has been clearly implicated in the pathogenesis of continuing HIV infection, and has been suggested to be involved with the causation of HFV Dementia. Perispinal delivery of etanercept results in delivery of a therapeutic amount of etanercept to the brain and the cerebrospinal fluid, resulting in improvement in AIDS Dementia. Chronic treatment is required. Etanercept delivered to the perispinal area at a usual dosage of 25–50 mg per week is given, delivered by percutaneous injection, usually once or twice per week, or by catheter delivery to the perispinal or epidural area via an implanted catheter with a remote reservoir, usually contained in the abdominal area.

10. Administration of a TNF binding biologic by intranasal administration to improve cognitive function. An alternative delivery method to allow a TNF binding biologic, such as etanercept, onercept, and pegylated soluble TNF receptor type 1 to reach the CNS is by intranasal administration. Intranasal administration for treating neurological disorders of the brain, or for enhancing cognitive function in normal individuals, is particularly advantageous for molecules, such as onercept, which have a short half-life. For example to use onercept to treat Alzheimer-type pathology one would administer 10–25 mg of onercept per day in two to four divided doses, which would be delivered by two to four nasal sprays per dose. Etanercept, because of its longer half-life, could be delivered once or twice per day, or, in some cases as little as once or twice per week.

Dosages and Routes of Administration

The dosage of a cytokine antagonist used for perispinal administration will in general be 10% to 100% of the dosage used as a single dose for systemic administration. For example, if the usual dose when administered systemically is 25 mg, then the dose used for perispinal administration will usually be between 2.5 mg and 25 mg.

For treating the above diseases with the above mentioned TNF antagonists, these TNF antagonists may be administered by the following routes:

Etanercept may be administered subcutaneously in the human and the dosage level is in the range of 10 mg to 100 mg per dose, with dosage intervals as short as one day.

Etanercept may be administered epidurally in the human and the dosage level is in the range of 2.5 mg to 50 mg per week.

Etanercept may be administered peridurally in the human and the dosage level is in the range of 2.5 mg to 50 mg per week.

Etanercept may be delivered by intranasal administration in a therapeutically effective dose.

Etanercept may be administered by percutaneous injection into the interspinous space in the human and the dosage level is in the range of 10 mg to 50 mg per dose, with dosage intervals as short as two days.

Etanercept may be delivered by use of an indwelling epidural catheter, by either continuous, low dose administration or by intermittent administration. Either way the weekly dose of etanercept may range from 2.5 mg to 50 mg.

Onercept may be delivered by use of an indwelling epidural catheter, by either continuous, low dose administration or by intermittent administration. Either way the weekly dose of onercept may range from 50 mg to 200 mg.

Onercept may be delivered by use of an indwelling catheter whose tip is implanted in the perispinal (extrathecal) space, by either continuous, low dose administration or by intermittent administration. Either way the weekly dose of onercept may range from 50 mg to 200 mg.

Onercept may be administered by percutaneous injection into the interspinous space in the human and the dosage level is in the range of 50–100 mg per dose, with dosage intervals as short as daily.

Pegylated soluble TNF receptor type 1 may be administered in a therapeutically effective dose.

Etanercept may be delivered by use of an indwelling epidural catheter connected to a remotely implanted pump containing a reservoir of etanercept in solution. The weekly dose of etanercept delivered to the epidural space utilizing this device may range from 5 mg to 50 mg.

ADVANTAGES OF THE PRESENT INVENTION

Accordingly, an advantage of the present invention is that it provides for the delivery of etanercept to the epidural space as a new biologic treatment of humans with cognitive impairment; such that the use of etanercept will result in clinical improvement, or will slow progression of the underlying pathologic process.

Another advantage of the present invention is that it provides for etanercept delivered by anatomically localized administration, which, when compared to systemic administration, produces one or more of the following: greater efficacy; more rapid onset; longer duration of action; improved delivery to the CNS; or fewer side effects.

Another advantage of the present invention is that it allows use of a lower dosage of etanercept than is routinely administered for the treatment of other chronic illnesses (which is usually 50 mg per week). By administering etanercept either directly into the epidural space, or in close proximity to the epidural space less etanercept is needed to obtain a therapeutic response. This reduces cost and also may reduce the incidence of adverse effects.

Another advantage of the present invention is that it provides methods of administration of etanercept which result in improved delivery of etanercept to the CNS for providing suppression and inhibition of the action of cytokines in a human to improve cognitive function in patients with brain pathology.

Another advantage of the present invention is that it provides methods of administration of etanercept which result in improved delivery of etanercept to the CNS for providing suppression and inhibition of the action of TNF in a human to improve cognitive function in patients without brain pathology.

Another advantage of the present invention is that it provides methods of administration of TNF binding biologics, including onercept and pegylated soluble TNF receptor type 1, which result in improved delivery of the TNF binding biologic to the CNS for providing suppression and inhibition of the action of cytokines in a human to improve cognitive function in patients with brain pathology.

Another advantage of the present invention is that it provides for etanercept administered by specific methods for treating humans with neurological disorders causing cognitive impairment which due to etanercept's biologic action will produce clinical improvement in the patient and will give the patient a better opportunity to heal, slow disease progression, prevent neurological damage, reduce pain, or otherwise improves the patient's health.

Another advantage of the present invention is that it provides for etanercept delivered by perispinal administration, as the preferred route, for the treatment of neuropsychiatric disorders, including Alzheimer's Disease, idiopathic dementia, Pick's Disease, other forms of dementia in humans, mild cognitive impairment and traumatic brain injury.

Another advantage of the present invention is that it provides for etanercept delivered by retrograde venous flow through the vertebral venous system into the cranial venous system, thereby facilitating delivery of etanercept to the brain for therapeutic purposes.

Another advantage of the present invention is that it provides for etanercept delivered by retrograde venous flow through the vertebral venous system into the cranial venous system, thereby facilitating delivery of etanercept to the brain for therapeutic purposes by bypassing the blood-brain barrier which is present in the cranial arterial circulation.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A method for delivering a TNF antagonist to the brain of a human for treating Alzheimer's related dementia, comprising administering the TNF antagonist etanercept parenterally into the perispinal space of said human without direct intrathecal injection, and thereafter positioning said human in a Trendelenburg position, for delivery of said TNF antagonist etanercept to the brain via the human's vertebral venous system (VVS).

2. The method of claim 1, wherein said TNF antagonist etanercept is administered in a dosage which comprises sterile water without a preservative.

3. The method of claim 1, wherein said TNF antagonist is delivered to the brain of the human to perform one or more of the following: reduce inflammation or improve cognition.

4. The method of claim 1, wherein said administered etanercept bypasses the blood-brain barrier to reach the brain.

5. The method of claim 1, wherein the head of the human is maintained in the Trendelenburg position for five to ten minutes.

6. A method for delivering etanercept to a human with Alzheimer's related dementia, comprising: perispinally administering an amount of a TNF antagonist etanercept to the human without direct intrathecal injection, and wherein said perispinal administration results in retrograde delivery of the TNF antagonist etanercept to the brain via the human's vertebral venous system in an amount of TNF antagonist etanercept to the brain effective to treat Alzheimer's related dementia.

7. The method of claim 6, further comprising positioning the human in a Trendelenburg position after administering said TNF antagonist etanercept.

8. The method of claim 6, wherein said TNF antagonist etanercept is administered in a dosage of no greater than 100 mg.

9. The method of claim 6, wherein said TNF antagonist etanercept is administered in a dosage of no greater than 50 mg.

10. The method of claim 6, further comprising administering said TNF antagonist etanercept in multiple dosages, wherein said dosages are administered on a weekly basis.

11. The method of claim 6, further comprising administering said TNF antagonist etanercept on a daily basis.

12. A method of delivering the TNF antagonist etanercept to the brain of a human, comprising administering said etanercept into the perispinal space of the human without direct intrathecal injection, and thereafter positioning said human in a Trendelenburg position to enable said etanercept to reach the brain via the human's vertebral venous system (VVS).

13. A method of delivering the TNF antagonist etanercept to the brain of a human, comprising administering said etanercept into the perispinal space of the human without direct intrathecal injection, and then positioning the plane of said human's head below horizontal.

14. The method of claim 13, wherein the plane of said human's head is maintained below horizontal for five to ten minutes.

15. The method of claim 13, wherein said etanercept is delivered to the brain.

16. A method of delivering etanercept to the brain of a human, comprising administering said etanercept into the perispinal space of said human without direct intrathecal injection; and positioning of said human with the head downward below horizontal to facilitate retrograde flow of said etanercept to the brain.

17. The method of claim 16, wherein said etanercept is delivered to the brain.

18. A method for delivering the TNF antagonist etanercept to the cerebrospinal fluid of a human, comprising administering said etanercept parenterally into the perispinal space of said human without direct inthrathecal injection, and thereafter positioning said human in a Trendelenburg position for delivery of said etanercept to the cerebrospinal fluid.

19. A method for delivering a TNF antagonist to the brain of a human for treating mild cognitive impairment, Alzheimer's related dementia, or vascular dementia, comprising administering the TNF antagonist etanercept parenterally into the perispinal space of said human without direct intrathecal injection, and thereafter positioning said human in a Trendelenburg position, for delivery of said etanercept to the brain via the human's vertebral venous system (VVS).

20. The method of claim 19, wherein said administered etanercept bypasses the blood-brain barrier to reach the brain.

21. A method for delivering a TNF antagonist etanercept to the brain of a human for treating Alzheimer's related dementia, comprising administering the TNF antagonist etanercept parenterally into the perispinal space of said human without direct intrathecal injection, and thereafter positioning said human in a Trendelenburg position, for delivery of said TNF antagonist etanercept to the brain.

22. The method of claim 21, wherein said etanercept is delivered to the brain via retrograde flow of said etanercept in the vertebral venous system of the human.

23. A method for delivering a TNF antagonist etanercept to the brain of a human for treating mild cognitive impairment, Alzheimer's related dementia, or vascular dementia, comprising administering the TNF antagonist etanercept parenterally into the perispinal space of said human without direct intrathecal injection, and thereafter positioning said human in a Trendelenburg position, for delivery of said etanercept to the brain.

24. A method for delivering a TNF antagonist etanercept to the brain of a human for treating a TNF mediated dementia, comprising administering the TNF antagonist etanercept parenterally into the perispinal space of said human without direct intrathecal injection, and thereafter positioning said human in a Trendelenburg position, for delivery of said TNF antagonist etanercept to the brain via the human's vertebral venous system (VVS).

25. The method of claim 24, wherein said human has a TNF mediated dementia selected from the group consisting of mild cognitive impairment, possible Alzheixner's related dementia, probable Alzheimer's related dementia, Alzheimer's related dementia, senile dementia/Alzheimer's disease, and vascular dementia.

26. A method for delivering etanercept to a human with Alzheimer's related dementia, comprising administering said etanercept parenterally into the perispinal space of said human without direct intrathecal injection, and thereafter positioning said human in a Trendelenburg position.

27. A method for delivering etanercept to a human, comprising administering said etanercept parenterally into the perispinal space of said human without direct intrathecal injection, and thereafter positioning said human in a Trendelenburg position.

28. The method of claim 27, wherein said human has Alzheimer's related dementia.

29. A method for delivering etanercept to a human with Alzheimer's related dementia, comprising administering said etanercept parenterally into the perispinal space of said human without direct intrathecal injection; and then positioning the plane of said human's head below horizontal after administration of said etanercept.

30. A method for delivering etanercept to a human with Alzheimer's disease, comprising administering said etanercept parenterally into the perispinal space of said human without direct intrathecal injection, and thereafter positioning said human in a Trendelenburg position.

31. A method for delivering a TNF antagonist to the brain of a human for treating Alzheimer's related dementia, comprising administering the TNF antagonist etanercept parenterally into the perispinal space of said human without direct intrathecal injection, and thereafter positioning the plane of the human's head below horizontal, for delivery of said TNF antagonist etanercept to the brain.

* * * * *

UNITED STATES PATENT AND TRADEMARK OFFICE
CERTIFICATE OF CORRECTION

PATENT NO.          : 7,214,658 B2
APPLICATION NO. : 11/016047
DATED               : May 8, 2007
INVENTOR(S)     : Edward Lewis Tobinick It is certified that error appears in the above-identified patent and that said Letters Patent is hereby corrected as shown below:

On the Title Page Item (*) and Item 45

Column 1, line 10, delete: "This patent is subject to a Terminal Disclaimer."

Figure 2:
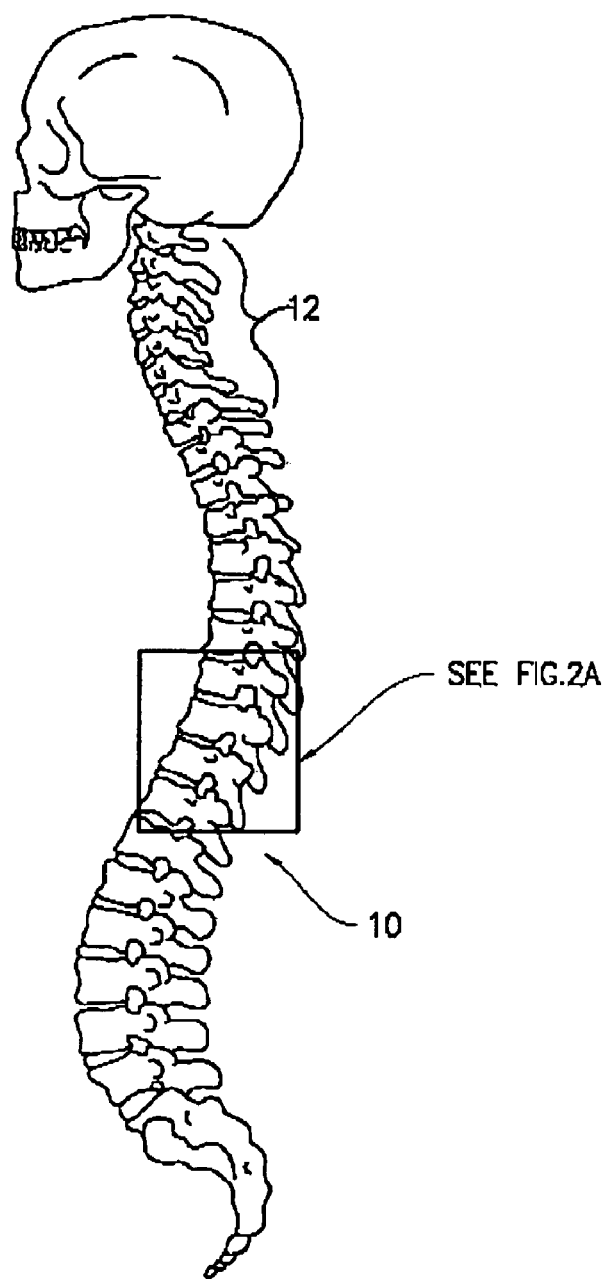
FIG. 2 is a diagram depicting perispinal administration, in accordance with the present invention.
Figure 2A:
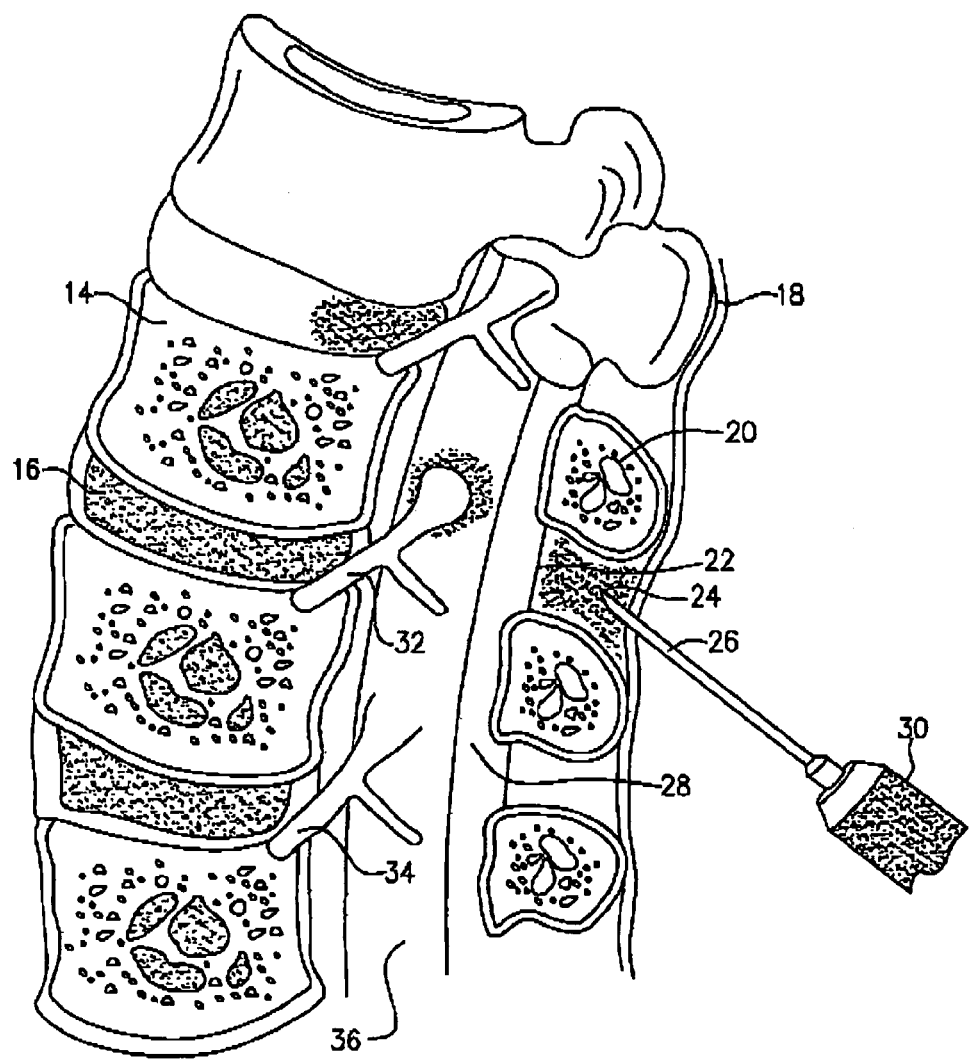
Figure 3A:
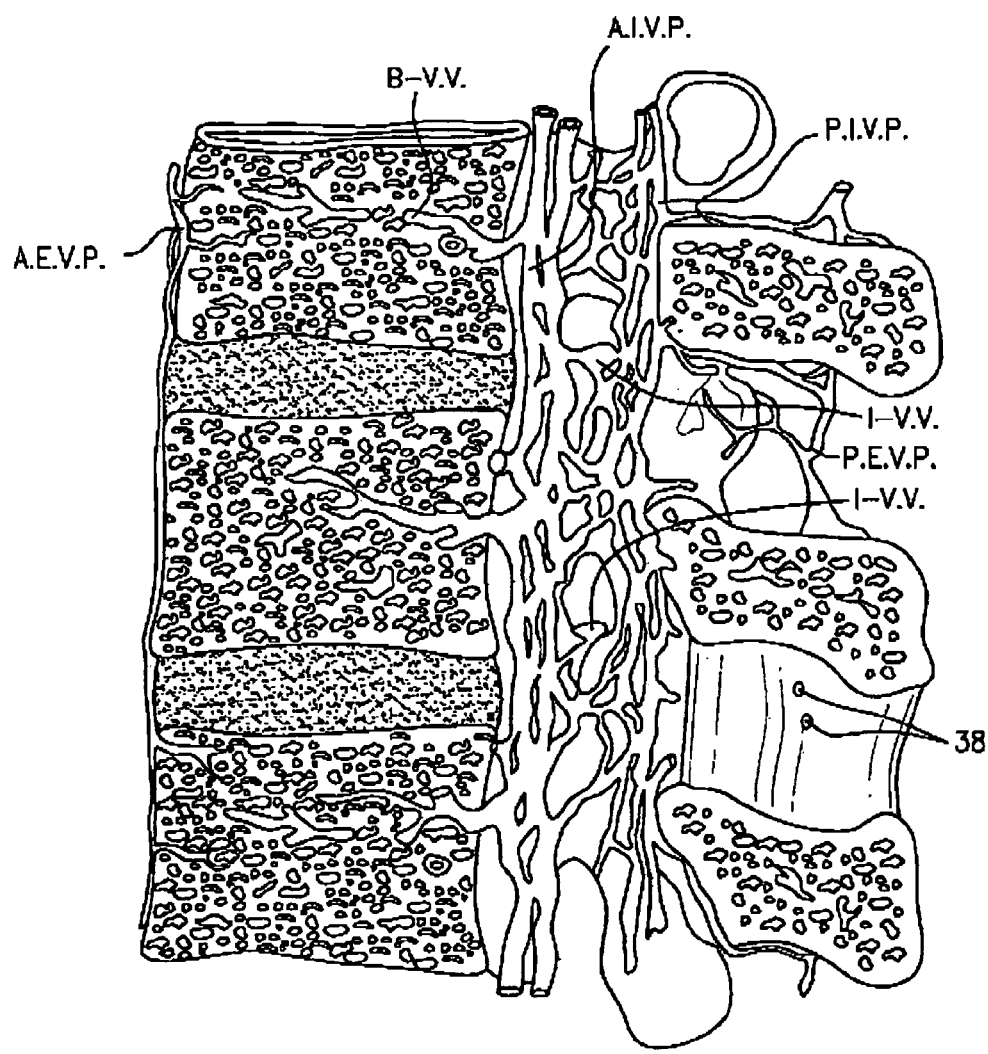
FIG. 3 are drawings by Frank Netter, MD depicting three different anatomic views of the vertebral venous system (VVS) and its anatomic relationship to the interspinous space and other anatomic elements of the spine.
Figure 3B:
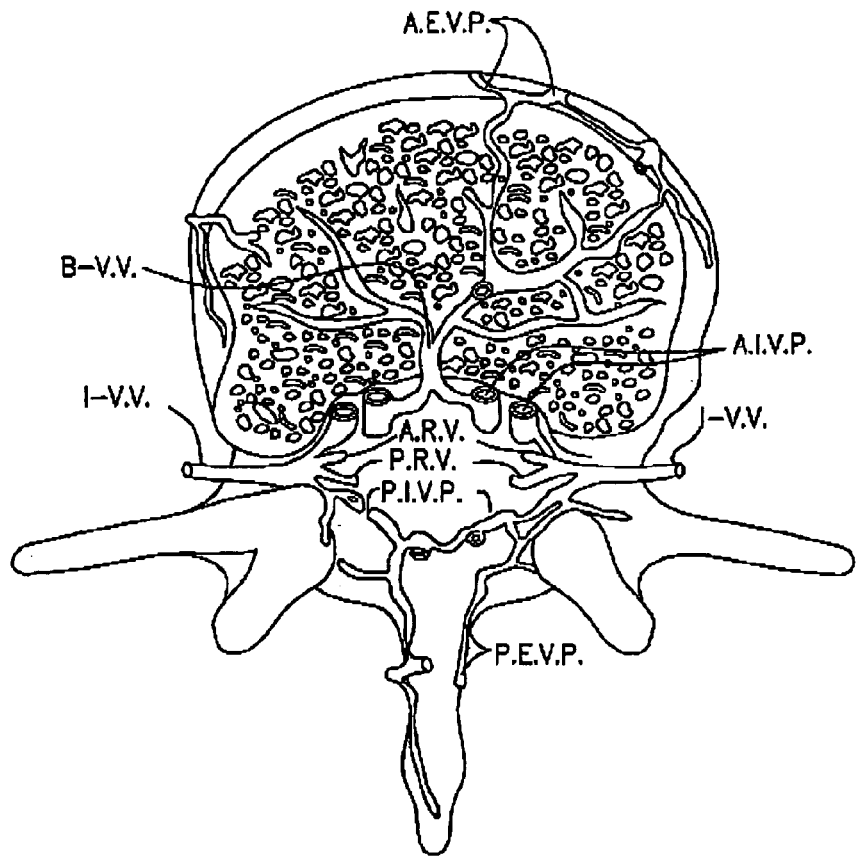
Figure 3C:
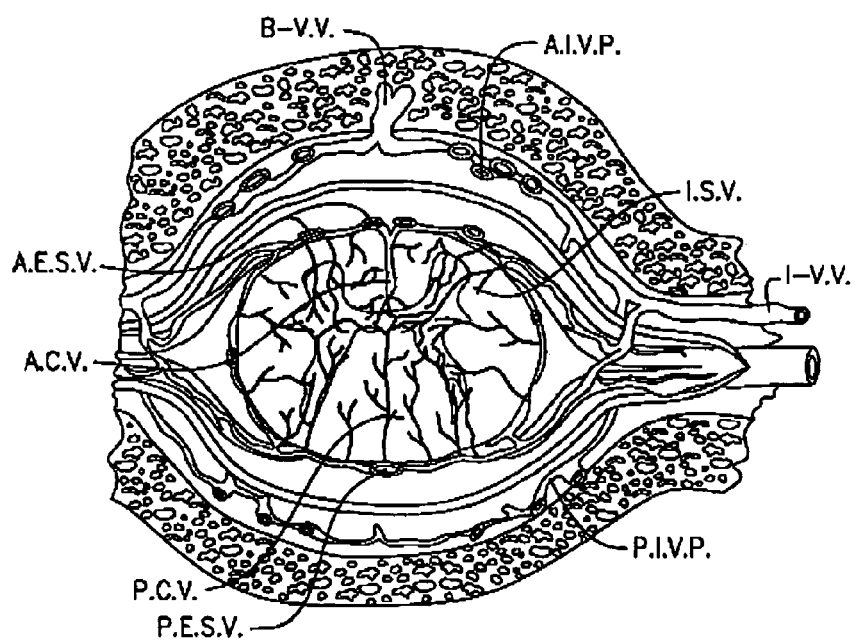

Column 11, delete lines 1 to 6, and replace them with the following:

-- Fig. 2 is a diagram showing the skull and spinal area;

Fig 2A is a diagram depicting perispinal administrating, in accordance with the present invention;

Fig. 3A is an enlarged elevational cross sectional view of the spinal area and the vertebral venous system (VVS) and its anatomic relationship to the interspinous space and other anatomic elements of the spine;

Fig. 3B is an enlarged horizontal cross sectional view of the spinal area and the vertebral venous system (VVS) and its anatomic relationship to the interspinous space and other anatomic elements of the spine; and Fig. 3C is an enlarged horizontal cross sectional view of the spinal area and the vertebral venous system (VVS) and its anatomic relationship to the interspinous space and other anatomic elements of the spine. --

Signed and Sealed this

Second Day of October, 2007

JON W. DUDAS
*Director of the United States Patent and Trademark Office*